United States Patent
Steinthal et al.

(10) Patent No.: US 7,034,677 B2
(45) Date of Patent: Apr. 25, 2006

(54) NON-SPECIFIC SENSOR ARRAY DETECTORS

(75) Inventors: Gregory Steinthal, Los Angeles, CA (US); Steven Sunshine, Pasadena, CA (US); Tim Burch, San Gabriel, CA (US); Neil Plotkin, Pasadena, CA (US); Chang-Meng Hsiung, Irvine, CA (US)

(73) Assignee: Smiths Detection Inc., Pasadena, CA (US)

( * ) Notice: Subject to any disclaimer, the term of this patent is extended or adjusted under 35 U.S.C. 154(b) by 94 days.

(21) Appl. No.: 10/624,194

(22) Filed: Jul. 21, 2003

(65) Prior Publication Data
US 2004/0135684 A1 Jul. 15, 2004

Related U.S. Application Data

(60) Provisional application No. 60/397,135, filed on Jul. 19, 2002.

(51) Int. Cl.
*G08B 1/08* (2006.01)
*G08B 19/00* (2006.01)

(52) U.S. Cl. .............. 340/539.12; 340/539.3; 340/539.11; 340/539.26; 340/511; 340/521; 340/333; 702/22; 702/60; 422/119; 600/300; 600/301; 128/903

(58) Field of Classification Search ........... 340/539.12, 340/565, 539.13, 539.26, 539.3, 539.11; 600/300, 301; 128/903, 904
See application file for complete search history.

(56) References Cited

U.S. PATENT DOCUMENTS 3,927,930 A 12/1975 Goldberg et al.
4,453,126 A 6/1984 Volgyesi
4,644,101 A 2/1987 Jin et al.
4,737,112 A 4/1988 Jin et al.
4,923,739 A 5/1990 Jin et al.
4,980,541 A 12/1990 Shafe et al.
5,104,210 A 4/1992 Tokas
5,200,334 A 4/1993 Dunn et al.
5,298,783 A 3/1994 Wu
5,429,975 A 7/1995 Sheu et al.
5,451,920 A 9/1995 Hoffheins et al.

(Continued)

FOREIGN PATENT DOCUMENTS

WO   WO 97/14958 A1   4/1997

(Continued)

OTHER PUBLICATIONS

"BAE Systems—JCAD Chemsentry® Point Chemical Vapor Detector"; published on the Internet: http://www.airforce-technology.com/contractors/nbc/bae2/; Jul. 2003.

(Continued)

*Primary Examiner*—Donnie L. Crosland
(74) *Attorney, Agent, or Firm*—Foley & Lardner LLP

(57) ABSTRACT

Portable and wearable chemical detector devices, such as badges, that are analyte-general, rather than analyte-specific, and which provide an optimal way to notify and protect personnel against known and unknown airborne chemical hazards. The devices are advantageously low-cost, have low-power requirements, may be wearable and are designed to detect and alarm to a general chemical threat. A sensor device includes two or more sensor devices, a processing module coupled to each of the sensor devices and configured to process signals received from each of the two or more sensor devices to determine an environmental state; and a communication module that communicates information about the environmental state to a user.

49 Claims, 20 Drawing Sheets

U.S. PATENT DOCUMENTS

| | | | |
|---|---|---|---|
| 5,512,882 A | 4/1996 | Stetter et al. | |
| 5,571,401 A | 11/1996 | Lewis et al. | |
| 5,677,662 A | 10/1997 | Bresolin et al. | |
| 5,704,352 A * | 1/1998 | Tremblay et al. | 600/300 |
| 5,788,833 A | 8/1998 | Lewis et al. | |
| 5,814,524 A | 9/1998 | Walt et al. | |
| 5,959,529 A * | 9/1999 | Kail, IV | 340/539.12 |
| 5,963,369 A | 10/1999 | Steinthal et al. | |
| 6,017,440 A | 1/2000 | Lewis et al. | |
| 6,085,576 A | 7/2000 | Sunshine et al. | |
| 6,192,351 B1 | 2/2001 | Persaud | |
| 6,198,394 B1 * | 3/2001 | Jacobsen et al. | 340/573.1 |
| 6,236,951 B1 | 5/2001 | Payne et al. | |
| 6,330,464 B1 | 12/2001 | Colvin et al. | |
| 6,336,936 B1 | 1/2002 | Simhambhatla et al. | |
| 6,350,369 B1 | 2/2002 | Lewis et al. | |
| 6,422,061 B1 | 7/2002 | Sunshine et al. | |
| 6,537,498 B1 | 3/2003 | Lewis et al. | |
| 6,553,336 B1 * | 4/2003 | Johnson et al. | 702/188 |
| 6,560,471 B1 | 5/2003 | Heller et al. | |
| 6,606,567 B1 | 8/2003 | Grate et al. | |
| 6,627,154 B1 | 9/2003 | Goodman et al. | |
| 6,700,484 B1 | 3/2004 | Barthelomew et al. | |
| 6,711,423 B1 | 3/2004 | Colvin, Jr. | |
| 6,720,887 B1 * | 4/2004 | Zunti | 340/870.28 |
| 6,738,671 B1 * | 5/2004 | Christophersom et al. | 607/60 |
| 6,759,010 B1 | 7/2004 | Lewis et al. | |
| 6,773,926 B1 | 8/2004 | Freund et al. | |
| 6,823,717 B1 | 11/2004 | Porter et al. | |
| 6,842,877 B1 * | 1/2005 | Robarts et al. | 715/708 |
| 6,854,317 B1 | 2/2005 | Porter et al. | |
| 6,868,350 B1 | 3/2005 | Zimmermann et al. | |
| 2001/0016683 A1 * | 8/2001 | Darrow et al. | 600/347 |
| 2002/0123672 A1 * | 9/2002 | Christophersom et al. | 600/300 |
| 2002/0141901 A1 | 10/2002 | Lewis et al. | |
| 2002/0193076 A1 * | 12/2002 | Rogers et al. | 455/66 |
| 2003/0186461 A1 | 10/2003 | Boehr et al. | |

FOREIGN PATENT DOCUMENTS

| | | | |
|---|---|---|---|
| WO | WO 00/79243 A1 | 12/2000 | |

OTHER PUBLICATIONS

"Joint Services Lightweight Standoff Chemical Agent Detector (JSLSCAD)"; published on the Internet: http://www.globalsecurity.org/military/systems/ground/jslscad.htm; (Last modif. Jan. 31, 2003).

Avnir, D. et al.: "Enzymes and other proteins entrapped in sol-gel materials" *Chem. Mater.;* vol. 6, pp. 1605-1614 (1994).

Chen, Q. et al.: "Stability of oxidases immobilized in silica gels" *J. Am. Chem. Soc.;* vol. 120, pp. 4582-4585 (1998).

Dave, B.C. et al.: "Photochemical studies using organic-inorganic sol-gel materials" *Mat. Res. Soc. Symp. Proc.;* vol. 435, pp. 565-574 (1996).

Dias, M. B.; "Investigating the viability of MEMS vapor sensors for detecting land mines" *CMU-RI-TR-00-24;* The Robotics Institute, Carnegie Mellon University, Pittsburgh, PA; Oct. 2000.

Dutta, R. et al.: "Bacteria classification using Cyranose 320 electronic nose" *Biomed. Engin. OnLine;* vol. 1, No. 4; published on the Internet: http://www.biomedical-engineering-online.com/content/1/1/4; (Oct. 16, 2002).

Jeremic, A. and A. Nehorai: "Landmine detection and localization using chemical sensor array processing" *IEEE Trans. Signal Proc.;* vol. 48, No. 5; May 2000.

Keller, et al.: "Electronic noses and their applications" *IEEE Northcon/Techn. Appln. Conf.;* Portland OR; Oct. 12, 1995.

Keller, P. E. et al.: "Three neutral network based sensor systems for environmental monitoring" *IEEE Electro®/94 Int'l Conf.,* Boston, MA; Paper No. PNL-SA-24175 (May 10-12, 1994).

Lacey, R. E. and G. S. Osborn: "Application of electronic noses in measuring biological systems" *ASAE Meeting Presentation at the 1998 ASAE Annual Int'l Meeting,* Orlando, FL; Paper No. 98/6116 (Jul. 12-15, 1998).

Lan, E.H. et al.: "HEME proteins encapsulated in sol-gel derived silica glasses and their reactions with ligands" *Mat. Res. Soc. Symp. Proc.;* vol. 330, pp. 289-294 (1994).

Li, Y.: "The Cyranose Chemical Vapor Analyzer"; published on the Internet: http://www.sensorsmag.com/articles/0800/56/main.shtml; (Aug. 2000).

Livage, J. et al.: "Immunoassays in sol-gel matrices" *J. Sol-Gel Sci. Technol.;* vol. 7, pp. 45-51 (1996).

Miller, J.M. et al.: "Synthesis conditions for encapsulating cytochrome c and catalase in $SiO_2$ sol-gel materials" *J. Non-Crystalline Solids,* vol. 202, pp. 279-289 (1996).

Oullette, J.: "Electronic noses sniff out new markets" *The Industrial Physicist;* Feb. 1999; pp. 26-29 (1999).

Pope, E.J.A. et al.: "Bioartificial organs I: Silica gel encapsulated pancreatic islets for the treatment of diabetes mellitus" *J. Sol-Gel Sci. Technol.;* vol. 8, pp. 635-639 (1997).

Rosch, W.: "Nosing out terrorism" Extremetech.com, published on the Internet: http://www.extremetech.com/print article/0,3998,a=16730,00.asp; (Oct. 18, 2001).

Skelley, D. S.: "E-nose technologies promise new diagnostic instruments" *IVD Technology Magazine;* published on the Internet: http://www.devicelink.com/ivdt/archive/00/01/004.html; (Jan. 2000).

Yamanaka, S.A. et al.: "Enzymatic activity of glucose oxidase encapsulated in transparent glass by the sol-gel method" *Chem. Mater.;* vol. 4, No. 3; pp. 495-497 (1992).

Yamanaka, S.A. et al.: "Nicotinamide adenine dinucleotide phosphate fluorescence and absorption monitoring of enzymatic activity in silicate sol-gels for chemical sensing applications" *J. Am. Chem. Soc.;* vol. 117, pp. 9095-9096 (1995).

Yamanaka, S.A. et al.: "Enzymatic activity of oxalate oxidase and kinetic measurements by optical methods in transparent sol-gel monoliths"*J. Sol-Gel Sci. Technol.;* vol. 7, pp. 117-121 (1996).

Mckennoch et al., "Electronic Interface Modules for Solid-State Chemical Sensors", 2002 IEEE, pp. 344-349.

Porter et al., "Sensor Based on Piezoresistive Microcantilever Technology", 2001, Sensors and Actuators A 88, pp. 47-51.

Zee et al., "MEMS Chemical Gas Sensor Using a Polymer-Based Array", Jun. 7-10, 1999, The 10th International Conference on Solid-State Sensors and Actuators, 4 pages.

Ziegler et al, Bioelectronic noses: a status report. Part II, 1998, Biosensors & Bioelectronics 13, pp. 539-571.

* cited by examiner

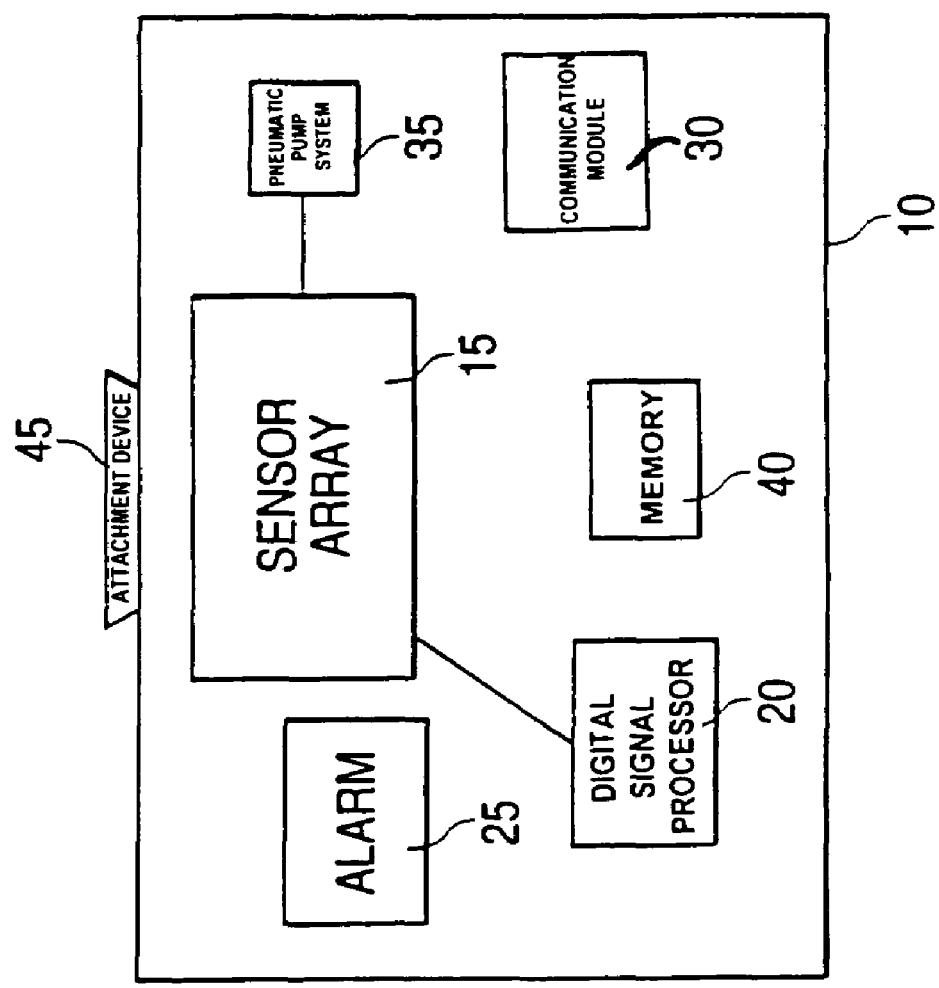

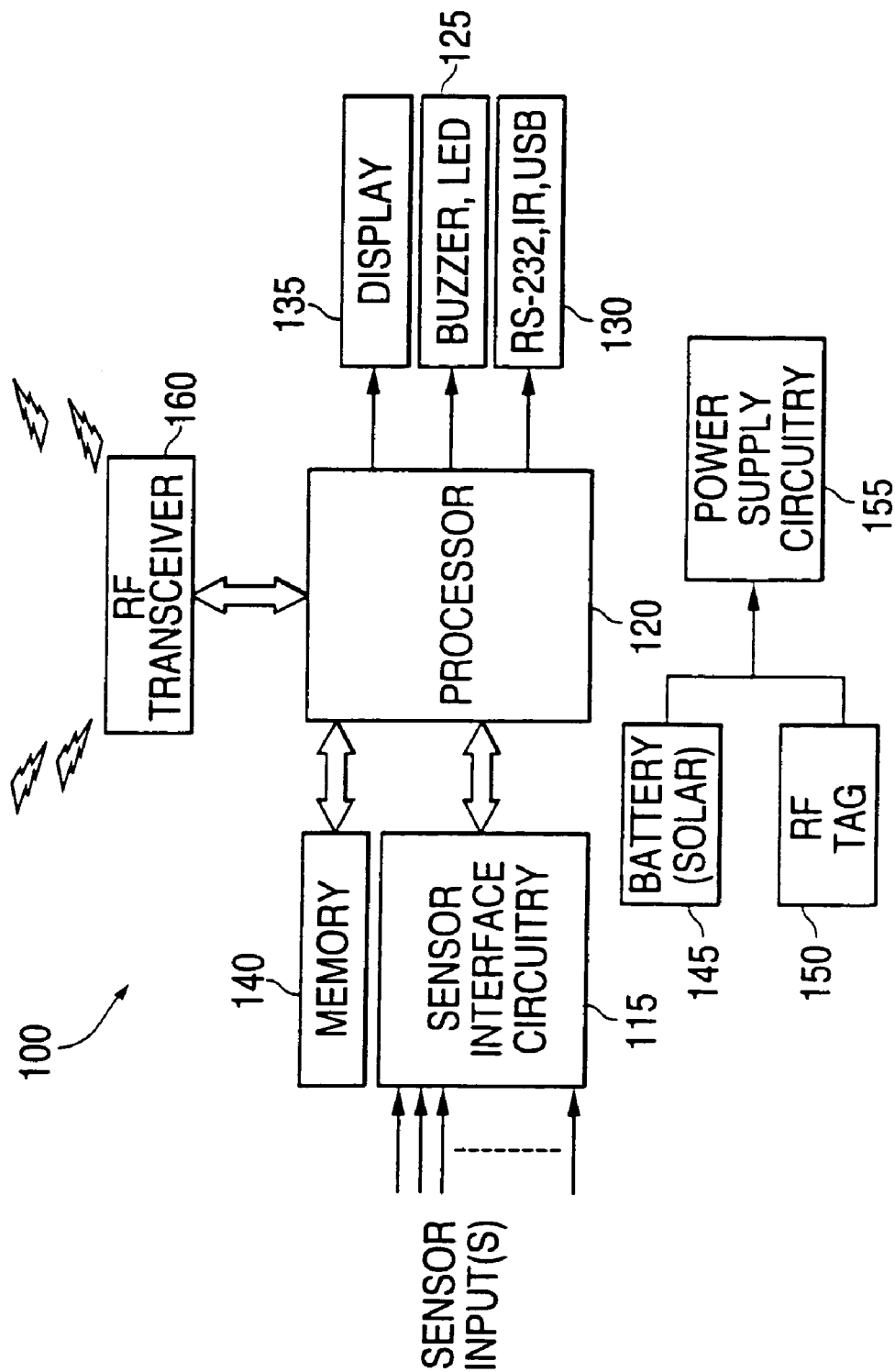

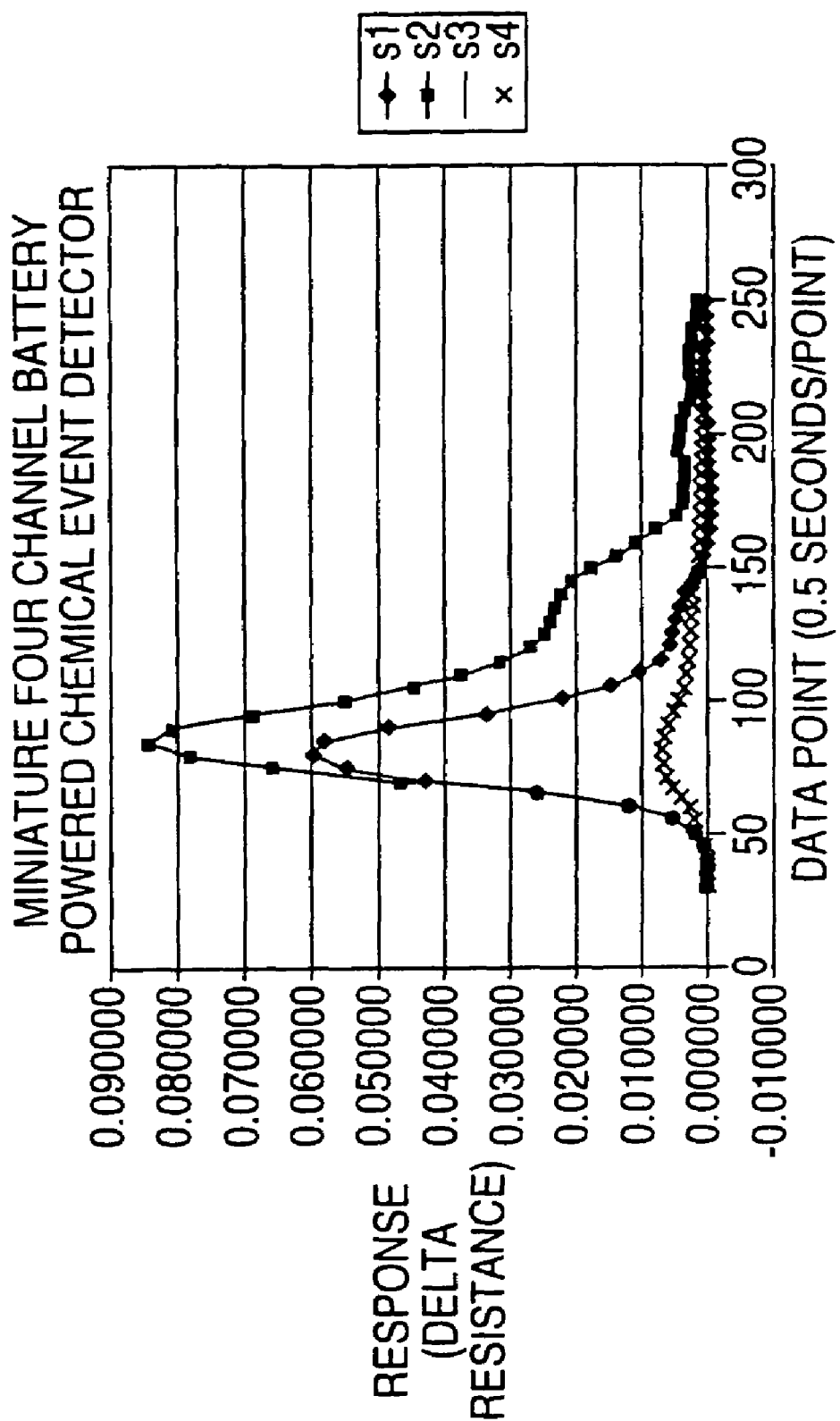

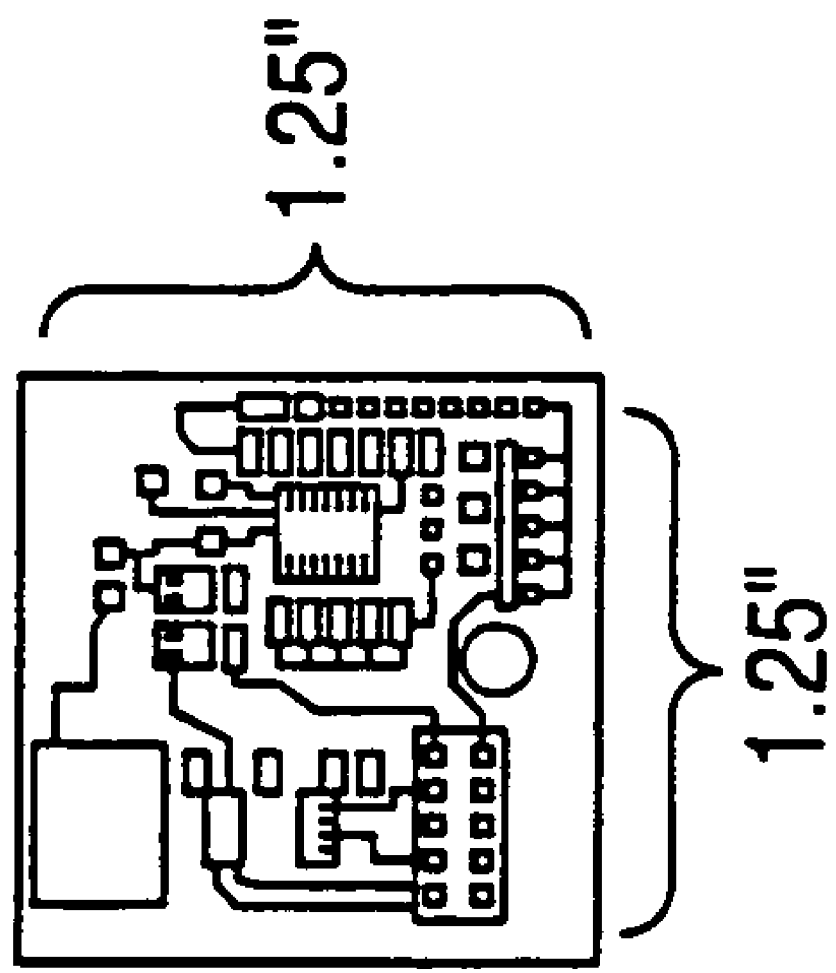

DISTRIBUTED SENSOR NETWORKS AND NOTIFICATION

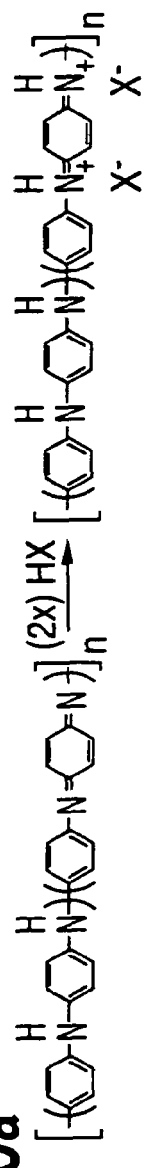
FIG. 19
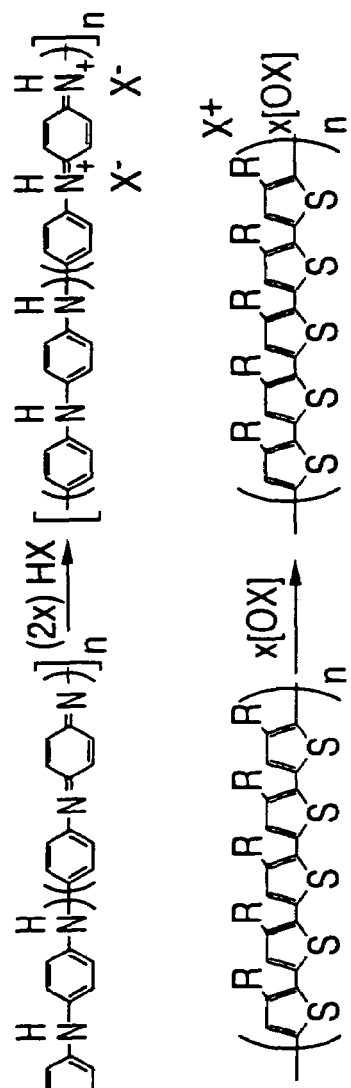
FIG. 20a
FIG. 20b
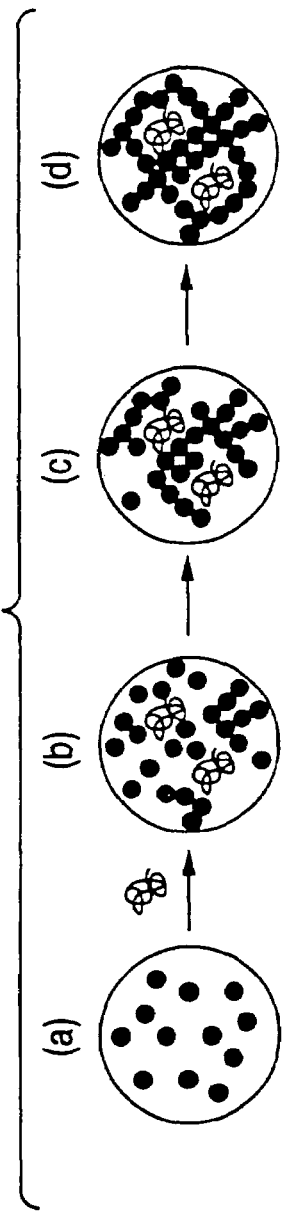
FIG. 21

NON-SPECIFIC SENSOR ARRAY DETECTORS

CROSS-REFERENCES TO RELATED APPLICATIONS

This application is a non-provisional of, and claims benefit of, U.S. Provisional Application Ser. No. 60/397,135, filed Jul. 19, 2002, entitled "Non-Specific Sensor Array Detector Badges", which is hereby incorporated by reference in its entirety for all purposes.

STATEMENT AS TO RIGHTS TO INVENTIONS MADE UNDER FEDERALLY SPONSORED RESEARCH OR DEVELOPMENT

NOT APPLICABLE

BACKGROUND OF THE INVENTION

The present invention relates to portable, handheld and wearable detector systems and in particular to portable, handheld and wearable detector systems including sensor arrays configured for non-specific chemical analyte detection, and which are configurable with software modules to detect and analyze a variety of environmental conditions and which have low operating power requirements and long lifetimes.

Civilian and military personnel, Coast Guard and Customs, State and Federal Emergency Responders, and Industrial Workers need a personal early-warning system to identify changes in environmental conditions, such as the release of hazardous airborne chemicals, in time to either evacuate or don protective equipment, such as chemical protective equipment (CPE). For example, releases of toxic industrial chemicals (TICs) may occur accidentally in the course of normal operations, from unseen leaks in fueling, heating or cooling systems, or from intentional hostile actions. Additionally, chemical warfare agents (CWAs) may be released during combat or in other potentially hostile situations. Each of these situations presents a unique and potentially broad range of chemical threats that typically cannot be identified a priori. There is a need to detect and characterize TICs, CWAs, and other environmental conditions before hostile exposure in order to take appropriate actions to neutralize the threat. A similar need exists after a TIC or CWA release to identify the chemical agent class such that appropriate defensive and decontamination measures may be taken.

While laboratory instruments with high specificity and accuracy are available, they are not generally suitable for field use because they lack physical robustness, require highly trained operators, and typically are not portable due to size, weight, high power consumption requirements, and chemical reagent (gases, liquids) requirements. In addition, specialized portable instruments for one threat type, (e.g. CWA) may not work for the other threat types of interest, (e.g. explosives, fire or TICs) or for improvised devices.

Handheld as well as wearable, passive detectors for hazardous conditions such as TICs and CWAs will greatly improve the safety of the personnel operating in threatened environments. Useful known portable detectors include point detectors and standoff detectors. One point detector, the Joint Chemical Agent Detector (JCAD), is hand held and portable but has a limited operational life on a single charge, requiring frequent recharging. In addition, the JCAD has to be handled impairing use of other devices simultaneously. Standoff detectors, such as the Joint Services Lightweight Standoff Chemical Agent Detector (JSLSCAD), can continuously protect personnel from CWAs, but (1) lack spatial resolution and (2) have detection limits much larger than the Immediately Dangerous to Health and Life (IDLH) level. General limitations of current badge or wearable detectors (e.g., SafeAir, ToxiRAE) include: 1) analyte-specificity: these require detailed a priori knowledge of chemical hazards, or multiple badges for broad spectrum coverage, and cannot detect new or unknown hazards; 2) single-use: disposable detectors and dosimeters require re-supply for continuous protection; 3) interpretation errors: calorimetric indicators require visual comparisons (color cards) that are prone to user subjectivity; 4) no alarm modes or communications capability: these do not provide rapid hands-free warning or transmission of status; 5) environmental performance: extremes of temperature (e.g., $<0°$ or $>40°$ C.) and humidity (e.g., $<10\%$ or $>90\%$ relative humidity (RH)) limit some sensors (e.g., electrochemical, conducting polymers). Such detectors also do not typically include datalogging capability (e.g., storing detailed historical information/records of the environment encountered), or may only provide a time-averaged history of exposure. Additionally, current detectors also typically have high operational power requirements and, therefore, typically short operational lifetimes. For example, the JCAD requires recharging or replacement of the power supply every 20 hours or less.

Some sensor devices, such as the ToxiRae Plus, produce audible and vibratory alarms, eliminate interpretation errors, and have datalogging capability, but these wearable sensors are still analyte-specific. In addition, these sensors are not useful as badge detectors since they require a pocket or belt clip due to their size and weight.

Wearable sensor devices with analyte-general capability have been developed, e.g., by EIC Laboratories, Inc. and Physical Sciences, Inc., however these devices have significant performance issues with humidity that are likely to affect the ruggedness and stability of the sensors during field-use of the badge detector.

There is therefore a need for personal detectors (e.g., portable and wearable detectors) that overcome the limitations of current detectors and which provide personnel with continuous, reliable protection in a potentially dangerous environment.

BRIEF SUMMARY OF THE INVENTION

The present invention provides portable and wearable detector devices, such as badges, that are analyte-general, rather than analyte-specific, and which therefore provide an optimal way to notify and protect personnel against known and unknown environmental conditions and events such as airborne chemical hazards without having to be handled. Such devices according to aspects of the present invention are advantageously low-cost, have low-power requirements, may be wearable and are designed to detect and alarm to a general environmental threat. Devices according to one aspect of the present invention include software modules configured to analyze sensor signals to provide for detection and identification of a variety of environmental conditions such as, for example, a release of TICs and CWAs. Such devices therefore advantageously allow for protecting more individuals, at lower cost and without specialized training, than expensive point detectors, stand-off area monitors, or existing detector badges that are limited to single chemical detection. According to another aspect, devices of the present invention include communication modules and are easily implemented in a network, such as a distributed network of sensor devices.

As used herein, an environmental event, condition or state may include, for example, an environmental parameter such as temperature, humidity or pressure, radiation level, or other physical stimuli, the presence or a level of an atmospheric constituent such as an airborn chemical or vapor, the presence or a level of a liquid or fluid constituent such as a chemical, a biological agent or material, a therapeutic agent, and others. A change in an environmental state or condition may include an increase or a decrease in the level or presence of an environmental parameter.

In certain aspects, detector devices of the present invention include one or more of the following features or attributes:

uses a non-specific sensor array to detect one or multiple environmental conditions, e.g., TICs and CWAs at IDLH levels,
uses polymer-composite sensors which are stable in the presence of moisture,
measures relative humidity and ambient temperature,
can be used in a wide range of operating conditions (relative humidity: 0–99% non-condensing; temperature: −15° C. to 40° C. or greater)
is passive and requires no user-interaction or user-attention during field-use,
includes downloadable flash memory to maintain an historical data record,
provides an audible alarm and inaudible alarm when TIC or CWA is detected,
includes an audible and inaudible periodic signal during normal operation,
is smaller than a credit card and weighs ounces,
has a battery lifetime of at least two weeks or more (e.g., multiple years) during continuous field-use,
has at least a two-year shelf-life,
meets the requirements for high-volume manufacturing,
has a low cost of goods and services (e.g., approximately $30 rough order of magnitude) for large volumes,
can be directly integrated into existing products (e.g., wireless sensor networks for detecting industrial chemical leaks and the release of CWAs in public facilities) to increase the available market size.

According to certain aspects of the present invention, polymer-composite sensor technology is used to construct arrays of two or more sensors useful for various applications, such as portable or wearable detector devices. for detecting and analyzing environmental conditions and changes therein such as the presence of TICs and CWAs. Such devices including PCS sensors are particularly advantageous as they can be configured to be compact, lightweight, wearable, rugged, stable, low-cost, low-power, and analyte-general. Polymer-composite sensors do not have the same humidity-performance limitations as conductive-polymer sensors. Since polymer-composite sensors are low-power sensors rather than no-power sensors (e.g., current off-the-shelf (COTS) badge detectors), detector devices according to certain aspects of the present invention are able to produce alarms with no interpretation errors and allow for datalogging capabilities. By combining a sensor array with techniques for detection and identification, detector devices according to certain aspects of the present invention are advantageously non-analyte-specific, addressing another limitation of current COTS detectors and others.

According to an aspect of the present invention, a sensor apparatus is provided. The apparatus typically includes two or more sensor devices, a processing module coupled to each of the sensor devices and configured to process signals received from each of the two or more sensor devices to determine an environmental state or condition, and a communication module that communicates information about the environmental state or condition to a user.

According to another aspect of the present invention, a wearable sensor device is provided. The device typically includes one or more polymer-composite sensors, an alarm, and a digital signal processor configured to monitor signals from the one or more sensors and provide an alarm activation signal to the alarm in response to a threshold condition. The threshold condition may be representative of a certain environmental state or condition or of a change in an environmental state or condition. An environmental event, condition or state may include, for example, an environmental parameter such as temperature, humidity or pressure, radiation level, the presence or a level of an atmospheric constituent such as an airborn chemical or vapor, the presence or a level of a liquid or fluid constituent such as a chemical, a biological agent or material, a therapeutic agent, and others. A change in an environmental state or condition may include an increase or a decrease in the level or presence of an environmental parameter.

According to yet another aspect of the present invention, an integrated sensor apparatus is provided that typically includes an array of two or more polymer composite sensors, a processing module coupled to each of the sensors and configured to process signals received from each of the two or more sensor devices to determine an environmental state, and a communication module that communicates information about the environmental state to a user.

According to still a further aspect of the present invention, a method of using a wearable badge detector is provided. The badge detector typically includes two or more sensor devices, a processing module coupled to each of the sensor devices and configured to process signals received from each of the two or more sensor devices to determine an environmental state, a communication module that communicates information about the environmental state to a user, and a power supply module for supplying power for the detector. The method typically includes providing the wearable badge detector to a user, attaching the detector to the user, and activating the detector, wherein once activated, the detector operates passively and continuously in excess of one week without requiring recharging or replacement of the power supply module.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIGS. 3a and 3b illustrate portable detection devices according to embodiments of the present invention.

FIG. 4 shows a typical response curve to a transient event.

FIG. 5 shows an example of a detector device according to an embodiment of the present invention.

FIG. 19 shows a table of four SMCB materials.

FIGS. 20a and 20b show the chemical structures of polyanilina and polythiophene, respectively.

FIG. 21 illustrates a sol-gel encapsulation process.

DETAILED DESCRIPTION OF THE INVENTION

Detector devices according to the present invention preferably include an array (i.e., at least two) of polymer-composite sensors. A polymer-composite sensor (PCS) typically includes a conducting media, a polymeric phase, and two electrodes. When a voltage is applied across the electrodes, electrons travel across the sensor via pathways consisting mainly of the conducting media, and sensor resistance is measured. Sensor resistance is one of the simplest measurements of the state of the sensor and is related to the number of molecules sorbed in the sensor—a change in sensor resistance is proportional to a change in the mass of sorbed molecules.

Figure 1A:
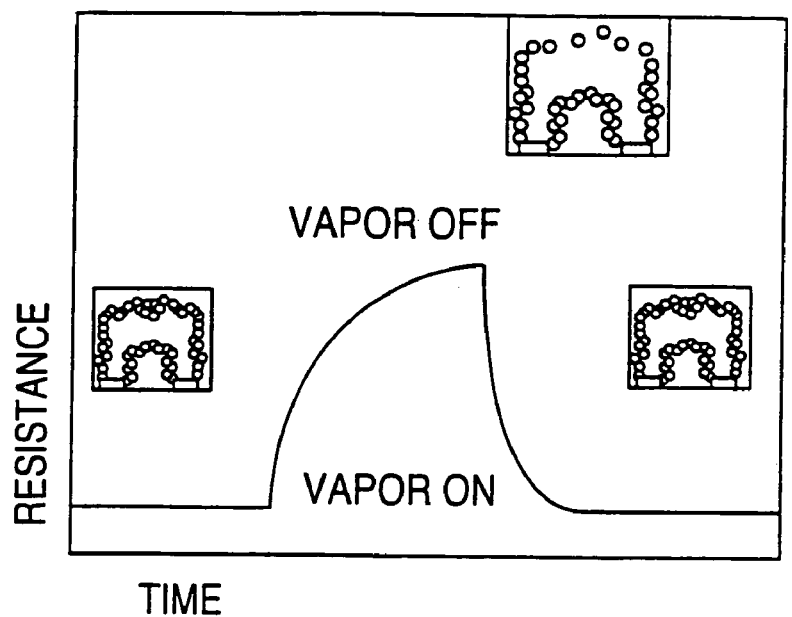
FIGS 1a and b illustrate a representation of a composite detector material responding during an analyte exposure, and a representation of how data are converted into response patterns, respectively according to an aspect of the present invention.

When there is a change in the chemical vapor that is in contact with a sensor, there is a concomitant response such as a change in sensor resistance. A change in the vapor phase causes a change in the chemical potential of its components and a subsequent difference in chemical potential between the sensor and the vapor phase. This difference in chemical potential results in a net transport of molecules into or out of the sensor, depending on whether the vapor or the sensor has greater chemical potential for that component. This net transport of molecules causes a change in the resistance since the number of sorbed molecules in the sensor changes, and the net transport continues until the chemical potential of all components is the same in the vapor and sensor. FIG. 1A shows a representative sensor response to a step change in the concentration of an analyte. For a period of time, the sensor is exposed to air and the sensor resistance, $R_{baseline}$, a is constant since the stimulus is also constant. The sensor is then exposed to a vapor ("vapor on") that contains air and an analyte that wasn't present during the baseline, causing an increase in the chemical potential of the vapor phase. Molecules of analyte travel from the vapor phase into the sensor, causing an increase in the number of molecules that are sorbed in the sensor and an increase in sensor resistance, R. When the sensor is no longer exposed to the analyte ("vapor off") and is exposed only to air again, analyte molecules desorb from the sensor and the sensor resistance decreases to the baseline resistance. The sensor response is calculated by:

$$\Delta R = (R - R_{baseline})/R_{baseline}. \quad [1]$$

Figure 1B:
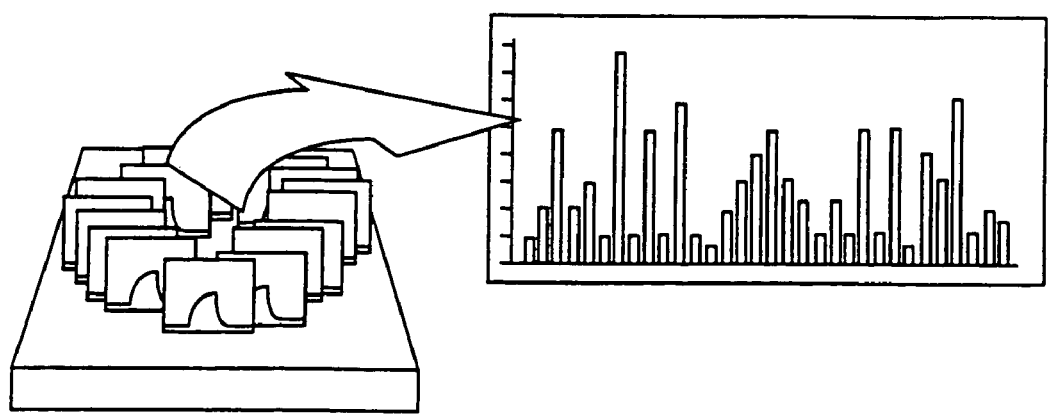

When a vapor is presented to an array of polymer-composite sensors, the array produces a pattern, as shown in FIG. 1B, since most, if not all, sensors in the array preferably produce different responses. The chemical potential of a vapor component is proportional to the percent saturated vapor pressure. (Percent saturated vapor pressure is equivalent to relative humidity for water content.) The chemical potential of a vapor component in the sensor is proportional to the number of sorbed molecules and is inversely proportional to the average interaction energy of the sorbed molecule with the sensor materials. A change in the sensor resistance is proportional to the change in the mass of sorbed molecules. At equilibrium, when the chemical potentials of each component in the vapor phase and the sensor are equal, the sensor response follows the scaling argument:

$$(\Delta R/R)_j \sim \sum_i \varepsilon_{ij} \Delta [P_i / P_{sat,i}(T_{sensor})]_i, \quad [2]$$

where $(\Delta R/R)_j$ is the sensor response for the $j^{th}$ sensor in the array, $\varepsilon_{ij}$ is the interaction energy between the $i^{th}$ component in the vapor and the $j^{th}$ sensor in the array, $P_i$ is the partial pressure of the $i^{th}$ component in the vapor, $P_{sat,i}$ is the saturated vapor pressure of the $i^{th}$ component in the vapor phase at the sensor temperature, $T_{sensor}$. Since the interaction energy, $\varepsilon_{ij}$, is different for each analyte-sensor pair, the response of each sensor in the array will be different for the same vapor. The interaction energy, $\varepsilon_{ij}$, is a measure of sensor sensitivity to a given analyte and in certain aspects has values ranging nearly two orders of magnitude for different analyte-sensor pairs. Although PCS sensors are preferred, it is understood that sensor devices according to the present invention may include other sensor types in addition to, or alternatively to, PCS sensors.

U.S. Pat. Nos. 5,571,401 and 5,788,833, each of which is hereby incorporated by reference in its entirety for all purposes, disclose chemical sensors useful for detecting analytes in a fluid (e.g., liquid, gas) as well as useful polymer-composite materials for polymer-composite sensor systems and devices.

In certain preferred aspects, an array of multiple, e.g., 32 sensors, is implemented in the devices of the present invention, but arrays can be comprised of fewer sensors or even more sensors as desired for the particular application. For certain specific applications, an array of only four or five sensors is typically sufficient if sensors are appropriately selected. In preferred aspects, an array of sensors includes a single PCS sensor or multiple PCS sensors. Also the array may include none, one or more other sensor types.

U.S. Pat. No. 6,085,576, which is hereby incorporated by reference in its entirety for all purposes, discusses aspects of an example of a handheld sensor system, which includes a relatively large number of sensors incorporated in a handheld device that is intended to be used for a wide range of applications. One such sensor, the Cyranose™ 320 (C320), is a COTS handheld vapor identification system that, in one aspect includes: (1) a polymer-composite sensor (PCS) array that returns a signature pattern for a given vapor, (2) a pneumatic system to present that vapor to the sensor array, and (3) implementations of pattern recognition algorithms to identify the vapor based on the array pattern. The C320 has been successfully tested as a point detector for TICs (e.g., hydrazine, ammonia, formaldehyde, ethylene oxide, insecticides) as well as CWAs (e.g., GA, GB, HN-3, VX).

FIG. 3a illustrates a portable detector device 10 according to an embodiment of the present invention. It is preferred that the housing structure is small Device 10 includes an array 15 of one or more sensors, preferably one or more polymer-composite sensors (PCS) as discussed herein. Digital signal processing (DSP) unit 20 receives and processes signals from sensor array 15 and stores data to memory 40. Pneumatic pump system 35 is optionally provided to assist with providing vapor to sensor array 15. In certain aspects, alarm module 25 is included to provide an active alarm when an alarm condition has been determined, e.g., when a programmable or preset threshold condition or value is exceeded. Alarm 25 can include a light such as an LED, a vibration module and a sound emitting module, e.g., including a speaker. One or more communication modules 30 are provided for interfacing with external intelligence such as a central alarm system. In one aspect, a communication module 30 includes an interface device such as an RF transmitter (or transceiver) for transmitting RF signals to an external device such as a command system or relay node. Communication module 30 can also include a receiving device such as an RF antenna (or transceiver) for receiving commands and data. Other useful interface types include IR transmitters, Bluetooth, RS-232, USB and Firewire interfaces, and any other wireless and physical connector interfaces (and associated protocols) for interfacing with external intelligence devices and systems such as a computer system. U.S. Pat. No. 6,422,061, which is hereby incorporated by reference for all purposes, discloses handheld sensor systems configured to interface, e.g., wirelessly, with a distributed network.

All components of device 10 are preferably coupled via one or more busses, but they may be individually directly connected as suitable for particular applications. In wearable badge device embodiments, an attachment device 45 such as a clip, strap or a pin is provided for attachment to a pocket, shirt lapel, belt, around the neck, etc as is convenient or necessary for the particular application. A battery and battery status monitor (e.g., LED light) are also preferably included (but not shown).

FIG. 3b illustrates a portable detector device 100 according to another embodiment of the present invention. In preferred aspects, device 100 is portable, wearable, has low power requirements and is self-calibrating. As shown, device 100 includes sensor interface circuitry module 115, which is configured to receive signals from a sensor array (not shown) and provide signals to a processor module 120 (e.g., DSP). Processor module 120 processes the received signals as will be discussed herein to detect and identify various environmental events or conditions. Memory 140 is used by processor module 120 to store various data, parameters and algorithms associated with event detection and identification. RF transceiver module 160 is configured to transmit and receive information to and from an external intelligence source such as a remote computer system, a base station or node in a distributed network of sensors, a remote alarm system, etc. Alarm module 125 includes one or more of a visual indicator such as an LED, an auditory indicator such as a buzzer or speaker and a vibratory indicator. Processor 120 activates alarm module 125 in response to detection and/or identification of an alarm event. An optional display 135 is provided to allow a user to view information related to event detection and identification processing. Communication module 130 is included to provide a communication path to external intelligence, whether directly connected (e.g., USB, Firewire, RS-232) or remotely connected (e.g., wireless). It will be appreciated that one or both of modules 160 and 130 may be implemented on detector device 100.

Power supply circuitry module 155 is provided to control various modes of operation of device 10. As will be described in more detail below, for example, power supply control circuitry is configured in certain aspects to place device 100 in a sleep mode, or reduced power consumption mode, and to awaken device 100 and place it in a full power consumption mode. Battery 145 is provided as a power supply source. Battery 145 may include a conventional battery, a solar cell or other power source. Alternatively, or in addition to battery 145, RF Tag module 150 is provided in some embodiments to allow for remotely powering up device 100 as will be discussed in more detail below. An attachment device (not shown) is also included in wearable device embodiments.

Devices 10 and 100, in certain aspects, are preferably implemented in or on a housing structure such as a card-shaped or badge-shaped plastic structure, or other compact structure allowing for ease of use, transport, wearability, attachment to a user, etc. Additional aspects of sensor devices of the present invention, such as sensor devices 10 and 100, including portability and wearability, low power consumption, self-calibration, and event detection and identification will now be described with particular attention to implementations including polymer-composite sensor (PCS) elements. It is understood, however, that sensor elements other than PCS elements may be additionally or alternatively used.

Sensor Interfaces

Referring to polymer-composite sensor arrays, a constant current source is provided to deliver constant low level dc current independent of the load. Studies indicate a significant reduction in sensor noise with bias currents less than 100 uA. Sensors have been shown to operate with as little as 5–10 uA. Also constant current provides a more accurate means to detect sensor response due to a high degree of linearity.

Low Power Consumption

Typical polymer-composite sensor elements exhibit a base resistance of between about 2 KOhms and about 100 KOhms, nominally about 10 KOhms. The peak power consumption (per sensor element) can easily be calculated (using a 10 uA constant current driving scheme) as follows:

$$Ppk=(10E\text{-}6)*(10E\text{-}6)*(10E3)=10\ nW$$

Further this number can be reduced if the sensors do not need to be constantly active. That is the average power:

$$P_{avg} = P_{pk} * DF$$

where DF is the duty_factor representing the percentage of the conversion time/response time. Conversion times represent the total time it takes to capture the sensor response and process the information. The conversion times are typically on the orders of msec's.

In one aspect, operation of devices of the present invention advantageously require less than about a milliwatt of power, and even less for certain device embodiments including only PCS sensors. The typical lifetime of a device operating at 1 milliwatt is on the order of approximately several weeks to several years or more. Further, power management capabilities reduce the power requirement as well as increase the lifetime of a power source.

Figure 22:
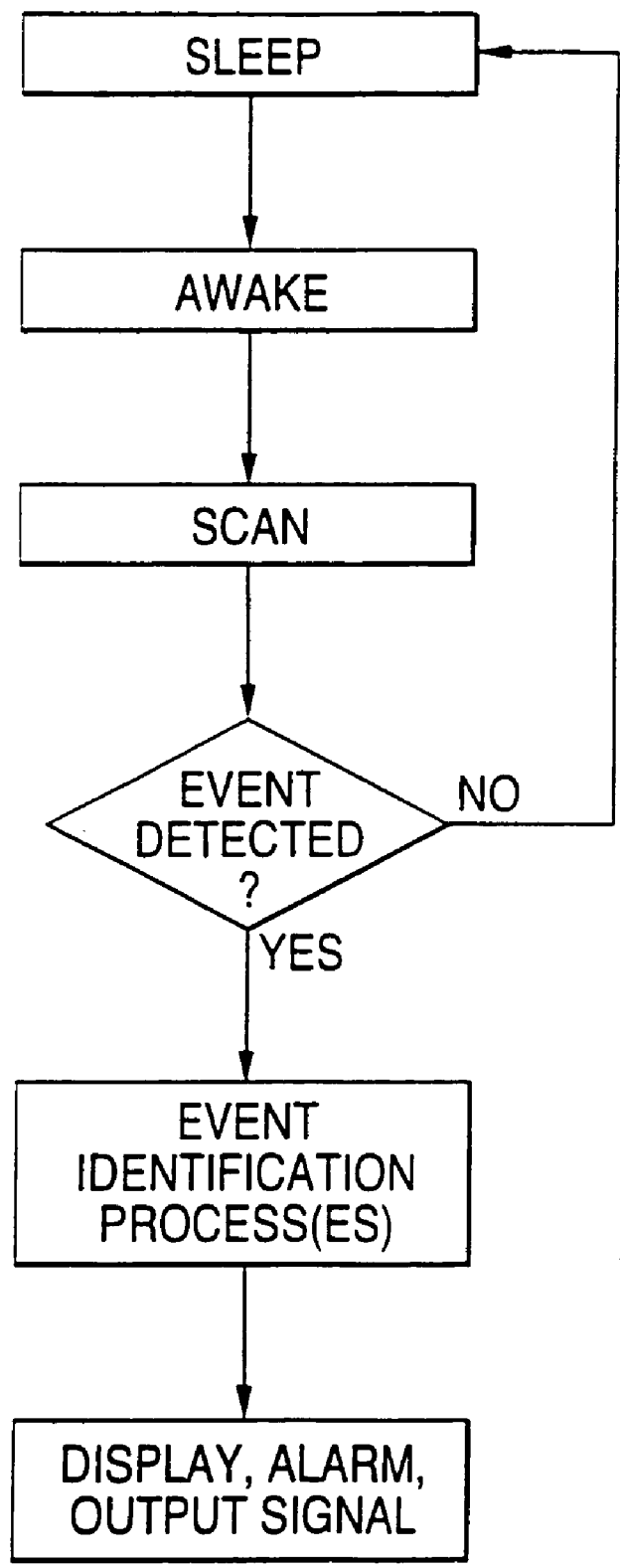
FIG. 22 illustrates a power management method according to one embodiment.

One goal of wearable badge devices is optimal power management. One embodiment of a power management method of the present invention is shown in FIG. 22. In one aspect, the device is placed in a SLEEP or very low power mode 200 for a significant amount of time, e.g., over 70%, or 80% or 90% of the time, depending on needed response time. The processor wakes up periodically 210, for example, in response to a wakeup signal from power supply circuitry 155, scans 220 across the sensor array and determines whether an event has occurred or is occurring 230. If not, the processor is put back to SLEEP 200. If an event is detected, the processor executes pattern recognition techniques 240 to identify the event. Once identified, the event is announced 250, e.g., either displayed, an output signal is activated, an audible alarm is activated, etc. or all of the above. Additional core average processing power is on the order of uA's.

Power Source

The device can be powered by a variety of means including an on-board battery or solar cell 145. Coin size batteries, such as standard 3 V batteries, are particularly useful and could last 5–10 years or more. The device might also be configured with an RF or IR tag element or module 150, whereby optical radiation or electromagnetic energy is remotely delivered to the device. In RF or IR tag embodiments, the device instantaneously stores enough energy to process information and relays this information back to the power source. Aspects of useful RF and IR tag circuitry can be found in U.S. patent application Ser. No. 60/477,624, filed Jun. 10, 2003, entitled "Chemical Passive Sensor", the contents of which are hereby incorporated by reference.

Self-Calibration

In certain aspects, the system is configured to periodically monitor all physical channels and determine if the sensor inputs are within the electrical operating range. If not, the system automatically biases each sensor accordingly and adjusts its baseline readings.

Event Detection

Event Detection is implemented to further reduce overall power consumption. In one aspect, an event first detected, then pattern recognition methods are used to identify the event(s). Event detection is threshold-based in one aspect. For example, in one aspect, once an event is detected the on-board processor is awakened (interrupted) and one or more pattern recognition processes are executed to identify the event.

Figure 23:
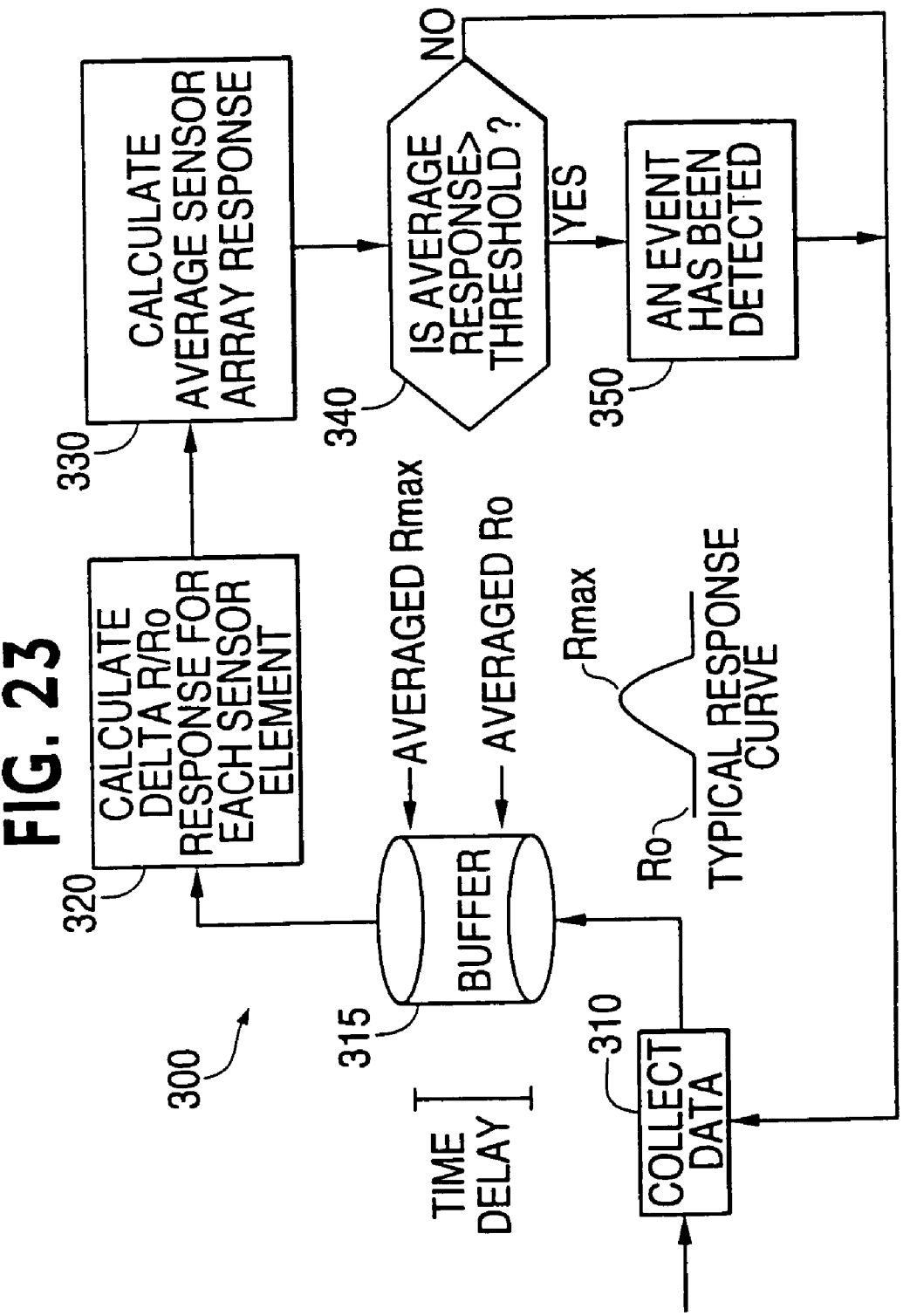
FIG. 23 illustrates a detection process and a typical response curve according to one embodiment.

FIG. 23 is a generic block diagram illustrating a detection process 300 and a typical response curve according to one embodiment. In the following description of aspects of process 300, process parameters such as delay time, average response and threshold have been chosen based on experimental results and are only meant to be exemplary and not limiting in any way.

Data is first collected 310 from each of the sensors, e.g., sensor response signals are collected. Each sensor response signal represents a resistive measurement in the case of PCS sensors. The resistance changes depending on the type of event to which the sensor is exposed. Each sensor element preferably responds in a different fashion. In one aspect, the process 300 allows for a moving base resistance; the response is the percent change from the most recent measurement with respect to a past moving base resistance. In one aspect, a circular buffered, backward-looking moving average process is coded and implemented in the on-board processor. The buffered data represents a time parameter to store the baseline resistance of each of the channels, e.g., number of sensors in an array.

The baseline resistance of all sensors is calculated 315. To account for slow changes in ambient conditions, such as humidity and temperature, and any sensor drift, the baseline resistance, $R_0$, is constantly updated based on recent history. There are at least two parameters—delay time and averaging time—that can be tuned. Since the data in one analysis was acquired over a short period of time, the delay time (or buffer) was set at 200 points (~2 minutes) and averaging time was set at 5 points.

The response of all sensors is calculated 320. In one aspect, the response, $\Delta R/R_0$, is calculated for all sensors as a fractional change in resistance, $$\Delta R / R_0 = \frac{R(t) - R_0}{R_0},$$

where R(t) is the time-averaged resistance at the present time and $R_0$ is the baseline resistance collected at 2 minutes earlier. The responses for individual sensors are used for pattern recognition to identify an event, e.g., determine whether a disturbance is a nuisance or a fire.

The sensor-averaged response is calculated 330. In one aspect, the sensor-averaged response, $(\Delta R/R_0)_{avg}$, is calculated to provide a robust measurement of the presence or non-presence of a disturbance.

The sensor averaged response is compared with a threshold value 340. In one aspect, for example, if $|(\Delta R/R_0)_{avg}| > 0.001$ (or other threshold value, e.g., 0.01), then the magnitude of the sensor-averaged response is too large indicating that an event has been detected, e.g., a disturbance from normal operation has been detected. The threshold value may be preset and adjustable. It is necessary to evaluate the magnitude of the disturbance since sensor responses increase and decrease with a change in an environmental state or in the presence of an environmental condition such as a fire. If no disturbance is detected, normal operation is continued.

Pattern Recognition

Once an event has been detected 350, the processor awakes from SLEEP (see, e.g., FIG. 22). The responses from all channels are temporarily stored in memory, e.g., RAM, and compared to known chemical patterns. Simple to very complex pattern recognition techniques might be implemented depending on the application. Such techniques include K-nearest neighbor (KNN), Canonical Discriminate Analysis (CDA), Soft Independent Modeling of Class Analogy (SIMCA), probabilistic neural network (PNN), artificial neural network (ANN), support vector machine (SVM), Fisher Linear Discriminate (FLD) and others.

In wearable badge embodiments, a detector badge would be worn by an individual, e.g., attached to a lapel or shirt or pants pocket with an integrated clip or pin, or worn around the neck, and when powered on would notify the wearer of normal detector status (e.g., green LED, no alarm) and battery status (e.g., green/red LED). After status check, the detector badge would monitor the environment continuously and announce detected hazard events, e.g., via an audible, visual (e.g., red LED) and/or vibratory alarm. Detector badges might also include modules for recording data and wirelessly transmitting information such as badge ID, status information and alarm condition information, to a central monitor station. Detector standardization using a supplied standard to verify proper operation, either periodically or before use, and battery replacement or recharging are typically user maintenance activities that may be required.

Wireless portable detectors without pneumatic system 35 can be implemented for applications that have stringent requirements for size, cost, power requirements and ruggedness. Such scaled down detectors are useful as badge detectors for TICs and CWAs. Additionally, communication module 30 can be eliminated for badge devices where a personal alarm is the only necessary feedback.

In certain aspects, a modular detector device is provided. For example, a detector device or sensor module may be coupled to a communication module. For example, a badge device in one aspect is configured to plug into a thin communications platform that allows the detector device to be included in a distributed network. The platform can include wireless or wired network connections. A sensor module can couple with any additional modules such as pnuemnatics, communication, calibration, power recharge and other modules. As another example, a detector device can be implemented as a residual life indicator, e.g., by inserting the device in a respirator cartridge as will be discussed in more detail below.

Event Detection and Analysis

In preferred aspects, digital signal processing (DSP) unit 20 incorporated in the detector device converts the sensor responses into an actionable answer. At least three different classes of techniques may be used, depending on the requirements of the application. These classes are listed in increasing order of complexity:

Simple detection: Thresholds are applied to individual sensors or globally to the responses of the entire array. When the threshold logic is satisfied, an alarm condition is detected. For example, if any of four sensors in an array exceeds a threshold value, an alarm activates, e.g., alarm 25 is activated.

Pattern recognition: The response pattern from the array is compared to patterns stored in a training set or library. When a match is found, the identity of the vapor is returned. Useful pattern recognition techniques include KNN, CDA, SIMCA, PNN, ANN, SVM, FLD and others.

Quantification: The response pattern from the array is used in certain aspects to calculate the concentration of analyte in the vapor phase.

In certain aspects these techniques can be used individually or mixed-and-matched. For example, simple detection can be used to detect that an event is occurring, and pattern recognition can be used after event detection to identify the nature of the event. Such a DSP methodology has been used successfully in a passive sensor array such as in a fire detector in UL and BSI laboratory tests.

For chemical events, the minimum detectable levels of the detector devices are important since the IDLH level has been identified as a requirement for consistently detecting the presence of TICs and CWAs. In certain aspects, the minimum detectable level (MDL) of a single sensor is measured by its detection limit. A detection limit is a useful concept to describe the performance of an analyte-specific sensor and is typically defined as the concentration that yields a sensor response with a signal-to-noise ratio equal to a threshold value (e.g., three). A detection limit is appropriate for analyte-specific sensors since few other chemicals could have caused the same level of response. If a detection limit is applied to a single sensor in an analyte-general array, any chemical could have caused the response since the sensor does not have specificity. Discrimination limits and identification limits are more useful concepts when describing the performance of an analyte-general sensor array. The discrimination limit is defined as the analyte concentration at which a method of pattern recognition can be used to discriminate an analyte in a carrier gas from the carrier gas alone. The identification limit is defined as the analyte concentration at which a method of pattern recognition can be used to consistently identify the presence of an analyte. An identification limit is preferably used as the measurement of performance for the MDL in certain aspects.

Figure 2:
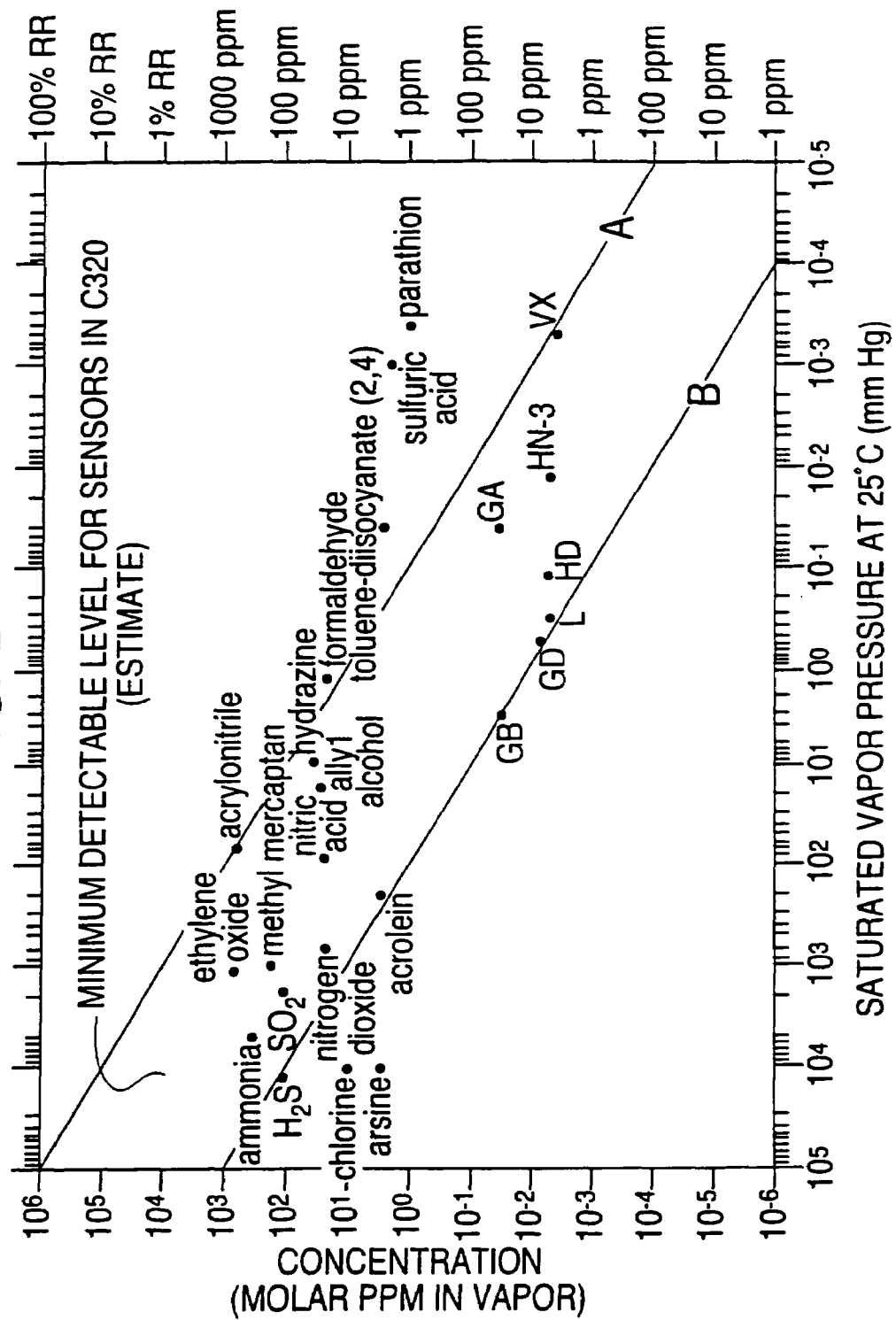
FIG. 2 illustrates IDLH levels of various agents.

Since equation (2) is valid for individual polymer-composite sensors, this equation can be used with experimental data for chemical species to estimate the MDL of the sensor array for any other chemical. FIG. 2 shows IDLH concentrations on a plot of concentration versus vapor pressure for CWAs and TICs. In FIG. 2, the sensor array has a high probability of identifying any analyte with a symbol above the region labeled "Minimum detectable levels for sensors in C320 (estimate)." This region will be called the region for minimum detectable levels (RMDL). The sensor array has moderate or low probability of identifying an analyte with a symbol inside or below the RMDL, respectively. The further below the RMDL, the probability of identifying the vapor decreases.

A region is preferably used for the MDLs rather than a single line for the following reasons:

Variability of environmental conditions: Applications that have environments that are more variable tend to have higher values for minimum detectable levels. The applications tend to have minimum detectable limits closer to line A.

Sample variability: Applications that have analytes with significant variability also have higher values for minimum detectable levels. These applications typically include natural products and tend to have minimum detectable limits closer to line A.

Application-specific sensor array: When a specific application is identified, specific sensors can be used (or sensor responses can be removed in software) to remove unimportant information, and sensor performance improves. Application-specific sensor arrays tend have lower values for minimum detectable levels closer to line B.

For badge detector devices, the MDL is generally closer to line B on FIG. 2. The two effects of variability are approximately equal and have opposite effects. Since a badge detector is a field-use device, environmental variability tends to increase the MDL, but sample variability is small since the chemicals are well defined, causing the MDL to decrease. Since applications tend to focus on CWAs and some TICs, the MDL can be improved by using the most appropriate sensor array for the application.

Tests of the C320 further validate the estimates in FIG. 2. During controlled tests of CWAs by independent laboratories (Midwest Research Institute and Battelle Memorial Institute), sensor arrays in the C320 detected Tabun (GA), Sarin (GB), Soman (GD), VX, Sulfur Mustard (HD) and Nitrogen Mustard (HN3) at or below a 9 ppbv threshold limit. Additional testing by the U.S. Army Edgewood Chemical and Biological Center showed the C320 correctly discriminated GB, GD, VX, HD, Malathion and DMMP.

Detector devices according to the present invention are also capable of identifying and discriminating narcotics, explosives (e.g., TNT, C4, RDX, ANFO and others) and hazardous materials.

Analyte-general chemical alert devices of the present invention are advantageously capable of detecting chemical hazard events arising from a wide range of chemical classes and are not restricted to a pre-defined short-list of just a few TICs. In certain aspects, effects of interference and cross-reactivity are minimized through a combination of sensor materials and detector operational design (algorithm and hardware) as described above using event detection, discrimination and interferent rejection techniques. 1) Event detection: Changes in environment (false positives) due to temperature, humidity, or chemical background occur gradually, over minutes to hours, and are not recognized as hazard events. Second, polymer-composite sensors (PCS) are not dosimeters; cumulative low-level exposure over hours/days will not trigger an alarm (unlike colorimetric indicators). Third, the polymer-composite (PCS) sensors are stable and less reactive to moisture than other sensors (e.g., conducting polymers). The combination of PCS sensors and event detection helps minimize false positive risks. 2) Discrimination: Real-time pattern-recognition techniques are preferably used to identify chemical classes. Although unrecognized chemicals may not register a class alarm (false negative), a two-stage approach minimizes the risk of false negatives by utilization of chemical event detection followed by discrimination. In this case, even new and unknown threat chemicals will register an event alarm for hazards above a threshold. 3) Interferent Rejection: In addition, real-time pattern recognition is preferably used to screen for and reject known interferents that may otherwise register as a chemical event, e.g., sudden increase in moisture content due to sea spray, spills or cleaning operations.

In wearable badge detector embodiments, polymer-composite sensor arrays are particularly advantageous as they are preferably 1) rugged and stable in various environments; 2) compact, lightweight and wearable; 3) inexpensive to produce; and 4) low power consumption systems. More detail about such advantages follows:

Rugged and Stable: Polymer-composite sensors are stable in the presence of moisture, allowing the sensor array to operate over a wide range of humidity (0–99%, noncondensing). PCS sensor arrays have been tested in aqueous solutions for nearly 5,000 continuous hours with no effect on sensor stability. The array also operates over a wide range of temperatures. Tests have been completed over a temperature range of −15° C. to 40° C. with no effect on the sensors. Finally, the array has a long shelf life. Sensor arrays have been stored for up to three years in an uncontrolled environment in a laboratory, and the arrays required no special pretreatment before use.

Compact, Lightweight, and Wearable: The chip can be implemented using dimensions of approximately 1.25"× 1.25"×0.25" with a mass of a few ounces. In preferred aspects, the chip, and hence the device in some embodiments, has a footprint area of less than about 4 square inches (e.g., 2"×2") and more preferably less than about 1 square inch (e.g., 1"×1"). The chip includes processors, battery, and sensors. Further miniaturization can be achieved, if required.

Inexpensive: The polymer-composite sensor array is inexpensive because the sensors are comprised of small amounts of carbon black and COTS polymers. The direct cost for sensor materials is very low, e.g., significantly less than $0.01.

Low Power: Polymer-composite sensors require only μW of power during normal operation. The chip can operate for at least six months or more using a typical battery.

In one embodiment, a four channel detector, operating in a variable humidity environment, detects transient chemical events (malodors) of unknown composition and triggers an alarm/response via an RF link when a programmable threshold value is exceeded. In one aspect, no data is transmitted from the sensor, just an alarm state. A typical response curve to a transient event is shown in FIG. 4 for such a device, and an example of such a device is shown as a square-shaped printed circuit board in FIG. 5; whereby the printed circuit board is preferably 1.25"×1.25" in size and whereby the backside contains the battery and the antenna. In a preferred embodiment, there is no pneumatic system and the detectors are continuously exposed to the environment.

Fire Detection and Prevention

Figure 6:
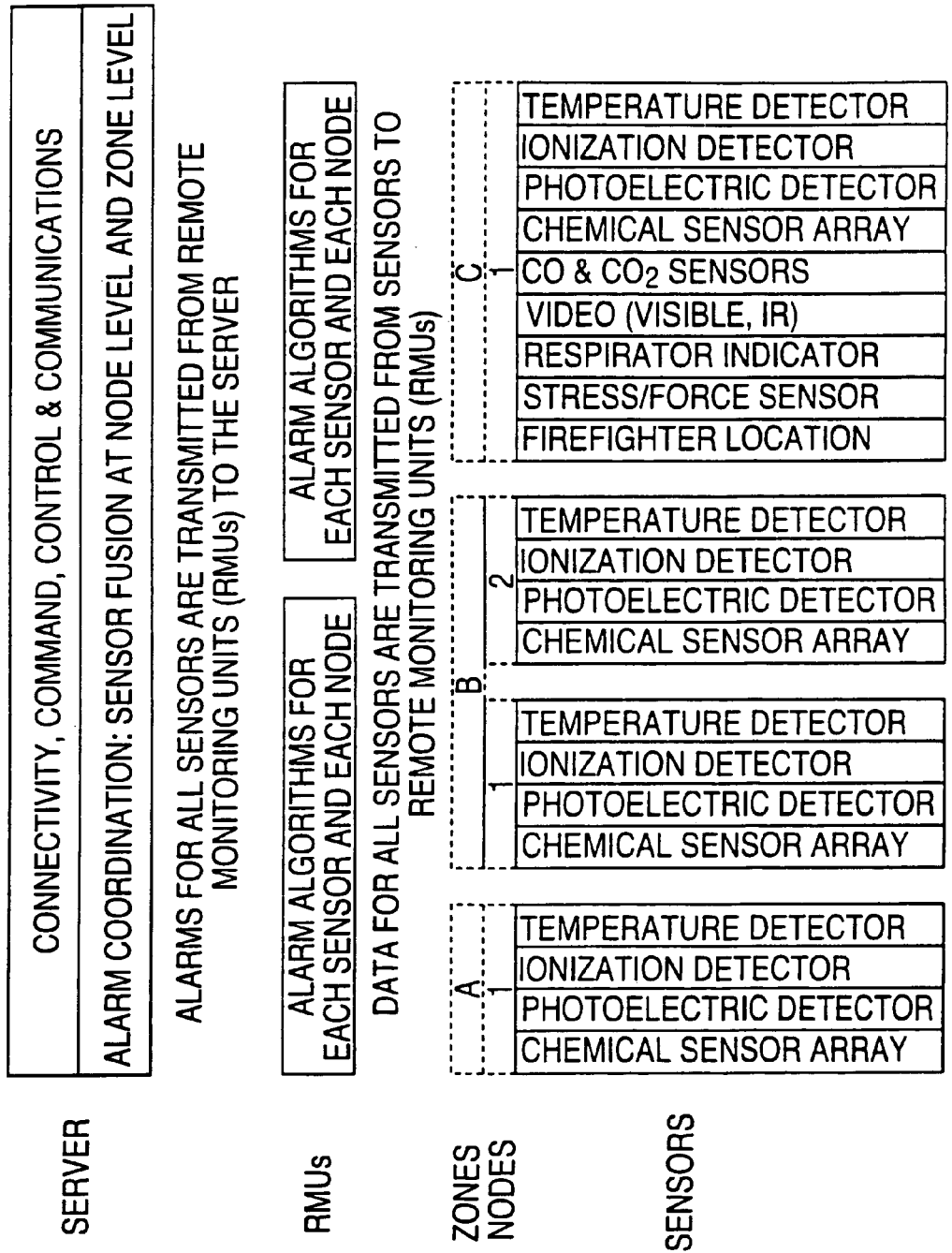
FIG. 6 shows an example of a fire detection system including detection devices according to an embodiment of the present invention.

In certain aspects, devices according to the present invention are particularly useful in fire detection and prevention activities. In such embodiments, devices of the present invention preferably include a PCS array and one or more additional sensor modules such as a photodetector, an ionization detection and a thermal detector. Published PCT Application WO00/79243, which is incorporated by reference for all purposes, discloses sensor systems including multiple sensor types which are useful for fire detection and prevention applications as well as for other detection applications as described herein. Signals from the PCS array and other included sensors are monitored and processed by an algorithm configured to detect events and nuisances and discriminate between fire sources and nuisance sources with a high degree of confidence so as to reduce the occurrence of false positives. FIG. 6 shows an example of a fire detection system architecture including detection devices according to an embodiment of the present invention. Nodes are defined as a collection of sensors/detectors at a single physical location. Zones are defined by physical relationships between nodes. The multi-level architecture for data analysis shown in FIG. 6 makes the system both flexible and scalable.

Many current chemical sensor arrays can discriminate different types of fires after the fire has been active for a long period of time. However, this use-model is not adequate for fire detection since time is of the essence. According to the present invention, an algorithm detects an event as early as possible and immediately identifies the event as a nuisance or fire. In the section following, examples of fire and nuisance data are disclosed:

Fire & Nuisance Data

TABLE 1

Fire tests that were completed in fire room.

| UL Fire Tests | BSI Fire Tests | Non-Standard Fire Tests |
|---|---|---|
| Gasoline 1 | Alcohol 1 | Dense plastic fabric |
| Gasoline 2 | Alcohol 2 | Flaming cotton fabric |
| Heptane 1 | Cotton 1 | Plastic curtain |
| Heptane 2 | Cotton 2 | Smoldering cotton 1 |
| Paper 1 | Flaming Wood 1 | Smoldering cotton 2 |
| Paper 2 | Flaming Wood 2 | Smoldering linen & plastic |
| Polystyrene 1 | Heptane 1 | Smoldering paper 1 |
| Polystyrene 2 | Heptane 2 | Smoldering paper 2 |
| Smoldering Wood 1 | Polyurethane 1 | Smoldering paper 3 |
| Smoldering Wood 2 | Polyurethane 2 | Smoldering cotton fabric |
| Wood Crib 1 | Smoldering Wood 1 | |
| Wood Crib 2 | Smoldering Wood 2 | |
| Smoldering | | |

TABLE 2

Nuisance tests.

| Series 1 | Series 2 |
|---|---|
| Bacon, open door | Bacon |
| Cigarette on pillow | Cigarette 1 |
| Floor buffing | Cigarette 2 |
| Fries cooking | Cigarette puffs |
| Oil, open door | Dry air freshener |
| Oil | Enamel |
| Sour craut | Nilotron |
| Steam | Popcorn |
| Sugar | Rustoleum |
| | Varnish |
| | Wall Paint |

In one embodiment, simple detection is used to detect that an event is occurring, and pattern recognition is then used to identify the nature of the event. This two-tiered algorithmic approach for detecting and identifying events works well for polymer-composite sensor arrays. The first algorithm simply detects that an event occurs. All fires must be detected, and, ideally, no nuisances would be detected. But it does not matter whether the event is a fire or a nuisance at this point because the second algorithm is used to differentiate between these two groups of events.

There are several parameters in the detection algorithm that are preferably optimized so that all fires are detected and a minimal number of nuisances are detected. These parameters include:
type and number of sensors used for averaging;
number of points used for time averaging;
number of points in the buffer (delay time);
the number of consecutive points outside the threshold; and
the value of the detection threshold.

Figure 7:
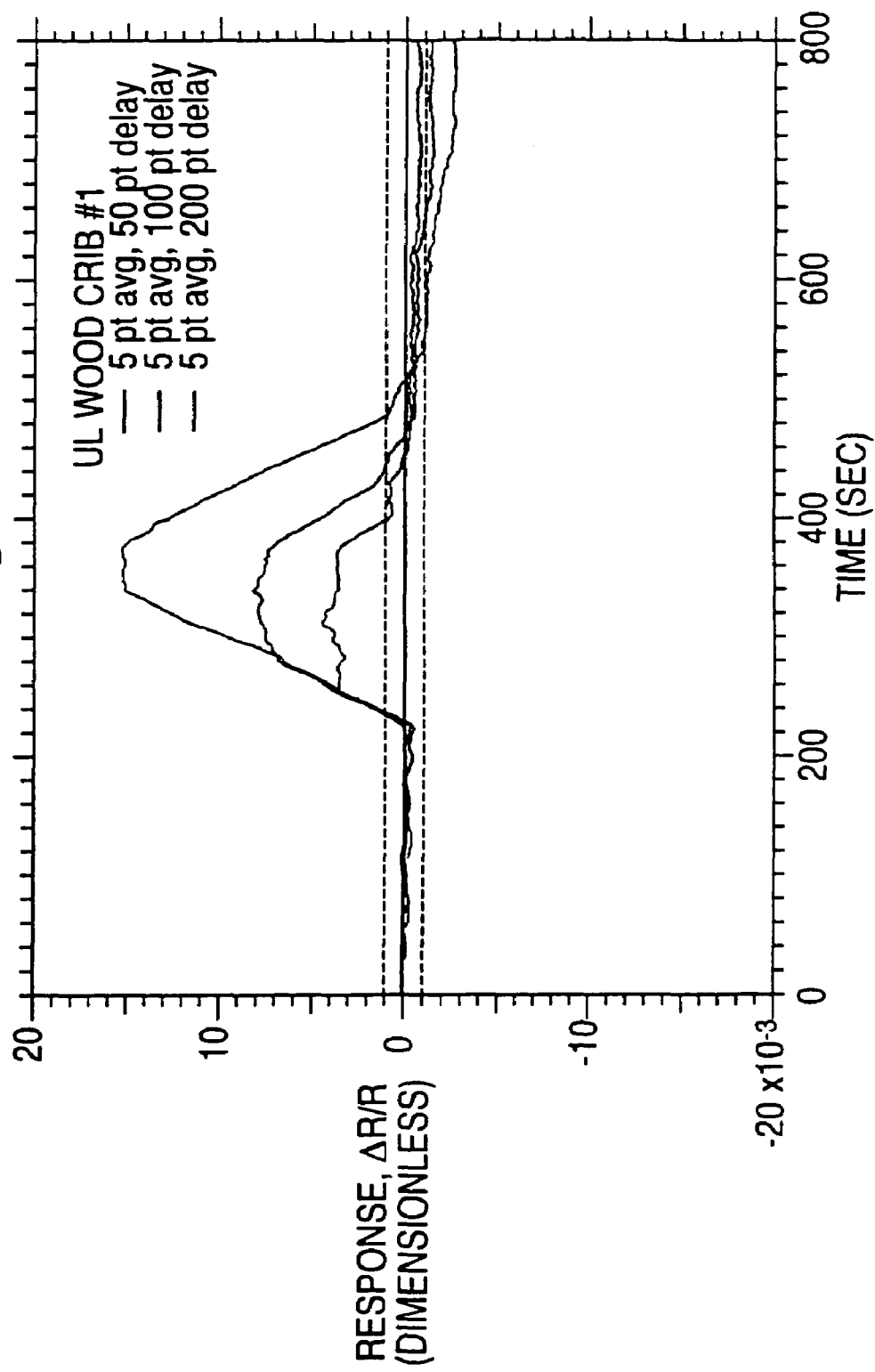
FIG. 7 shows a typical response for a device using 32 sensors.

A typical response is shown in FIG. 7 using an array of 32 PCS sensors when all 32 sensors are used and the number of points in the buffer is a parameter. The parameter had little effect on the detection time, but the number of buffer points drastically affected the overall magnitude of the response.

Figure 8:
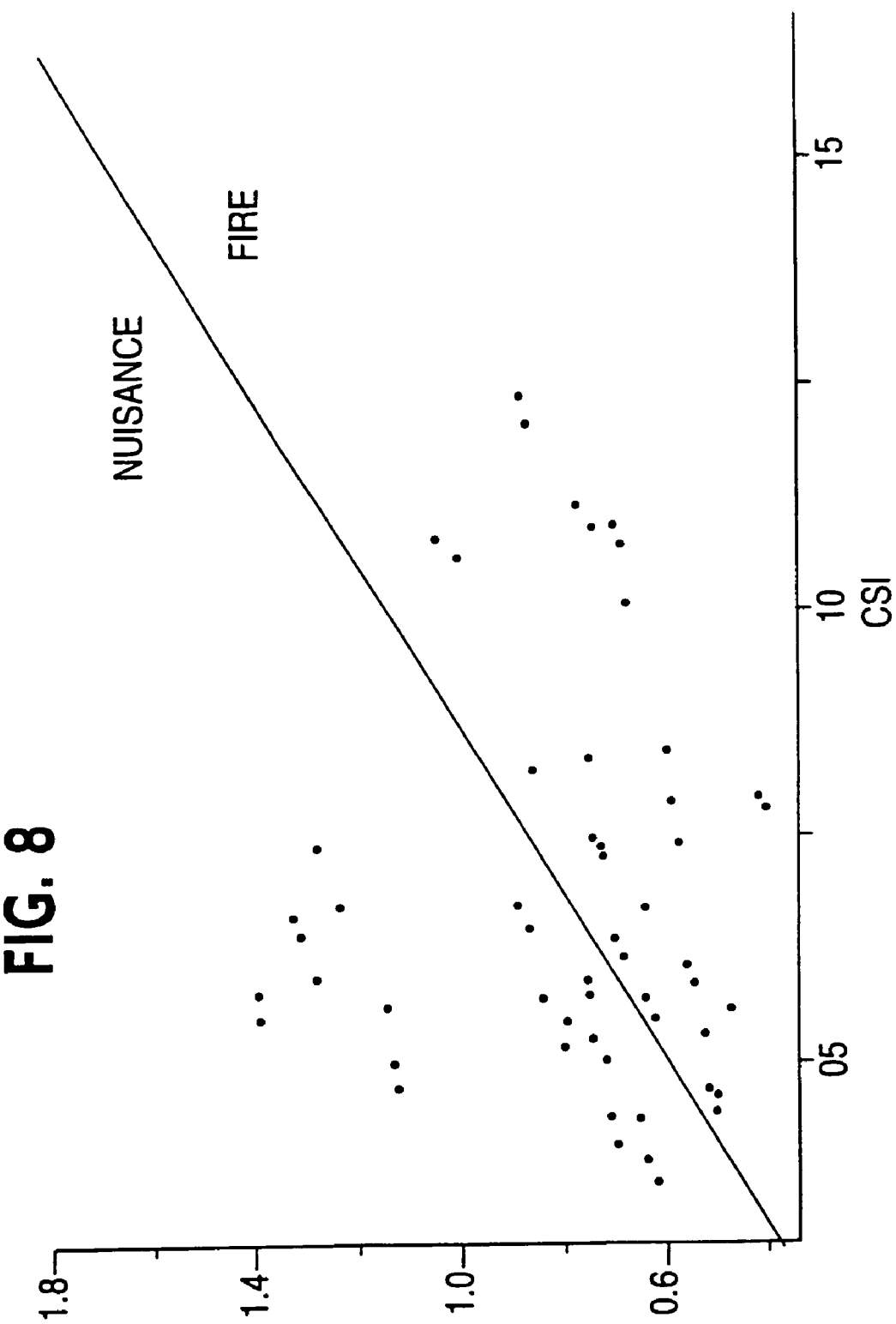
FIG. 8 illustrates a model using Soft Independent Modeling of Class Analogy (SIMCA).

Once an event is detected, the second part of the algorithm identifies the nature of the event as a fire or a nuisance. FIG. 8 illustrates a model using Soft Independent Modeling of Class Analogy (SIMCA). In particular, FIG. 8 shows the results for a SIMCA model for fire and nuisance tests that exceed the positive detection threshold. The line separating these two regions was drawn to minimize the number of false negatives, whereby a false negative corresponds to a case where the actual event is a fire but no alarm is sounded.

Additional useful algorithms are disclosed in U.S. patent application Ser. No. 10/112,151, filed Mar. 29, 2002, the contents of which are hereby incorporated by reference for all purposes.

Protective Absorption Based Filters

In certain aspects, devices of the present invention are useful in protective absorption based filter systems. The actual useful life of a protective absorption based filter is a function of the amount of absorbent material, the absorbent-sorbed species interaction, and the concentration and duration of the chemical exposure. Since this data is almost always unknown, the manufacturers' recommendations and civilian and military specifications are based on a few marker chemicals and test scenarios and offer only a rough guide as to when to replace or regenerate the filter. In most cases as well, the end user does not know when the exposure starts or ends, and what chemicals and concentration levels are present in the environment. Sensor devices of the present invention incorporated into a filter or pneumatic pathway can provide a timely warning to the user that the absorptive capacity of the filter has reached a pre-defined level. This allows users to exit the hazardous area and replace or regenerate the media and reduce the potential hazard to these personnel. Accordingly, in one aspect, the present invention provides polymer-composite sensor arrays in protective air filtration systems so as to provide low-cost, low power, lightweight, rugged, stable, and accurate residual life indicators for personal protective air filtration systems for Volatile Organic Chemicals (VOCs) and other hazardous materials. Such systems are useful in, for example, filter breakthrough systems, indoor air quality applications, cabin air systems, personnel protective equipment and motor vehicles.

In one embodiment, multiple miniature sensor devices are positioned at various depths in a filter bed such that successive sensor detection of a breakthrough event (at the IDLH) level and subsequent alarm outputs correspond to consumption of the absorptive capacity, hence indicating residual life. The final sensor is preferably placed appropriately to permit some exit time from the hazardous area without undue wastage of filter cartridges.

Figure 11:
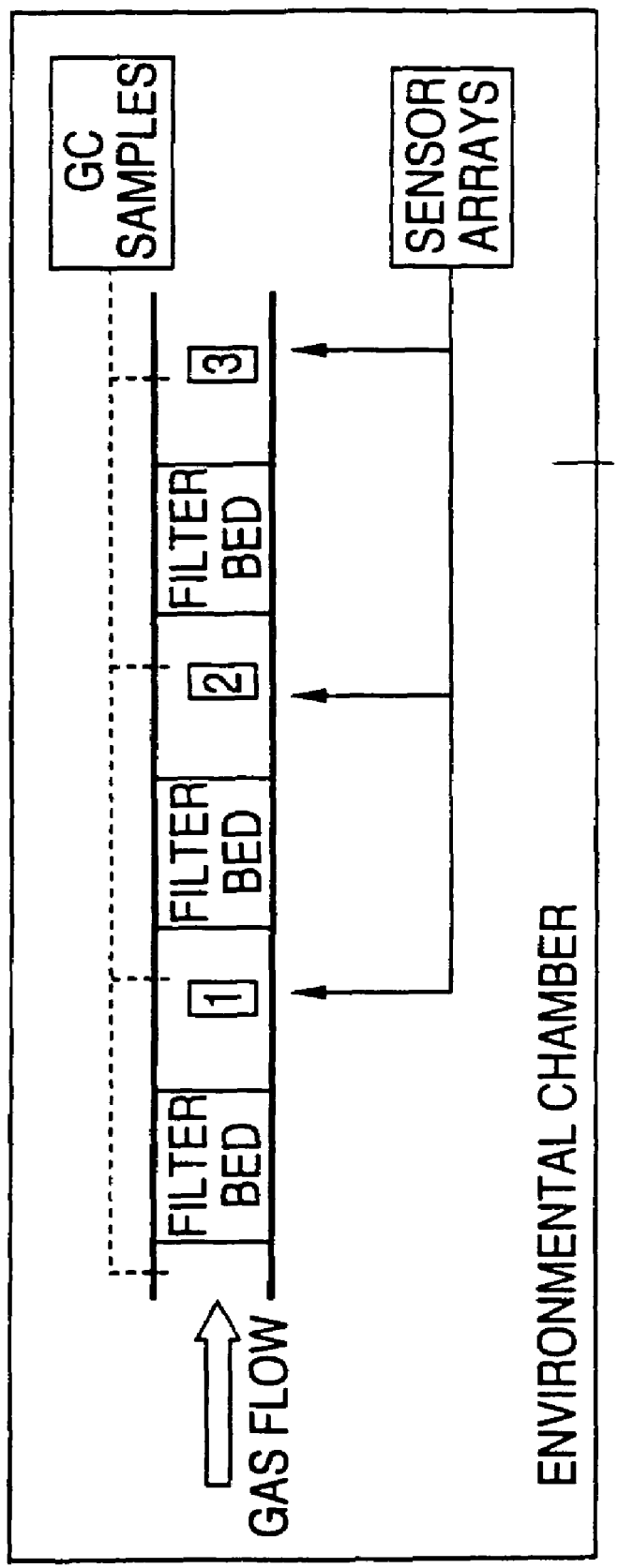
FIG. 11 illustrates a schematic representation of a Residual Life Indicator Fixture according to an embodiment of the present invention.

FIG. 11 illustrates a schematic representation of a Residual Life Indicator Fixture according to an embodiment of the present invention. As shown, detectors are sequentially positioned within a filter bed by embedding detectors in filter material in a gas flow path. Inlet and approximate stage-wise analyte concentration is monitored semi-continuously by Gas Chromatography and continuously by sensor output. The upstream sensor (1) responds to the presence of the analyte when the first Filter Bed experiences breakthrough while the still protected downstream sensors (2) and (3) do not respond. This is analogous to consumption of ⅓ of the filter system capacity (⅔ Life Remaining). As flow continues, downstream sensor (2) responds as the second Filter Bed experiences breakthrough; this corresponds to consumption of ⅔ of the filter system capacity (⅓ Life Remaining). The final filter bed also serves as the gas scrubber. The approximate stage-wise concentration in the filter bed is preferably monitored by Gas Chromatography as well as by the polymer-composite sensor system.

Figure 9:
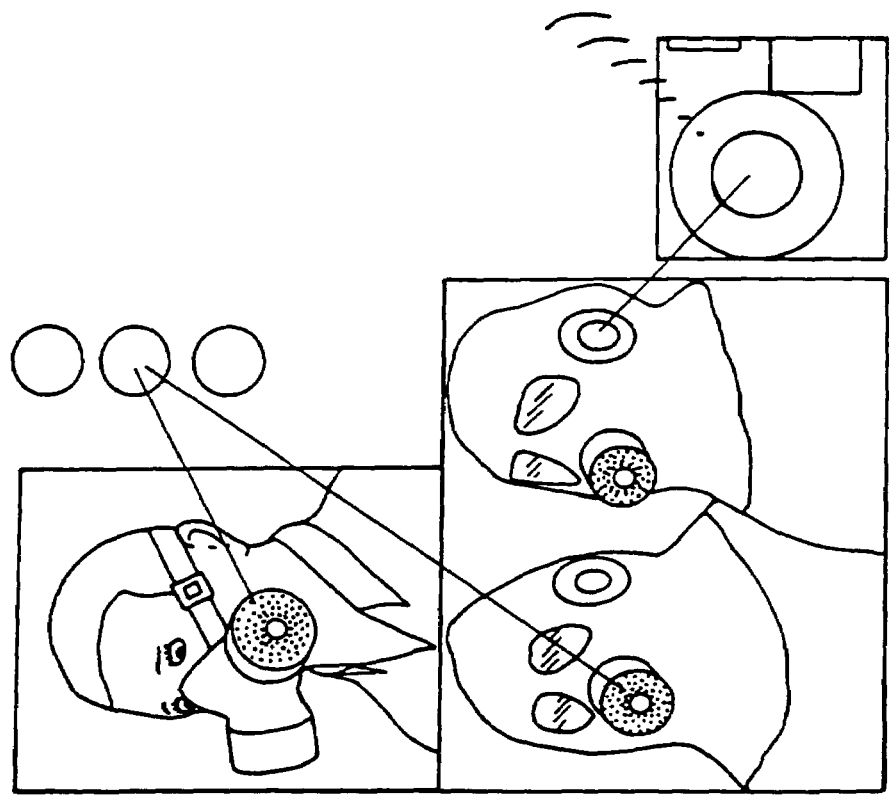
FIG. 9 llustrates examples of chemical filter systems for which an end-of-service-life indicator (ESLI) module including one or more PCS sensors are useful.

FIG. 9 illustrates examples of chemical filter systems for which an end-of-service life indicator (ESLI) module including one or more PCS sensors is useful. In particular, FIG. 9 shows gas masks having ESLI for chemical filters for military, homeland security and industry. Such uses may be for: forward-deployed personnel, weapons inspection, embassy/civilian personnel, first responders (fire department personnel, police department personnel, emergency management specialists), and hazardous chemical handling. When an alarm is detected, it is sent from an ESLI annunciator or wireless transmitter/receiver, which may be durable inside the mask, and the alarm information provided may include user ID, date and time. Each of the PCS sensors are preferably about 2 mm in size and are disposed in the filter bed of the chemical filter of the gas mask.

Figure 10:
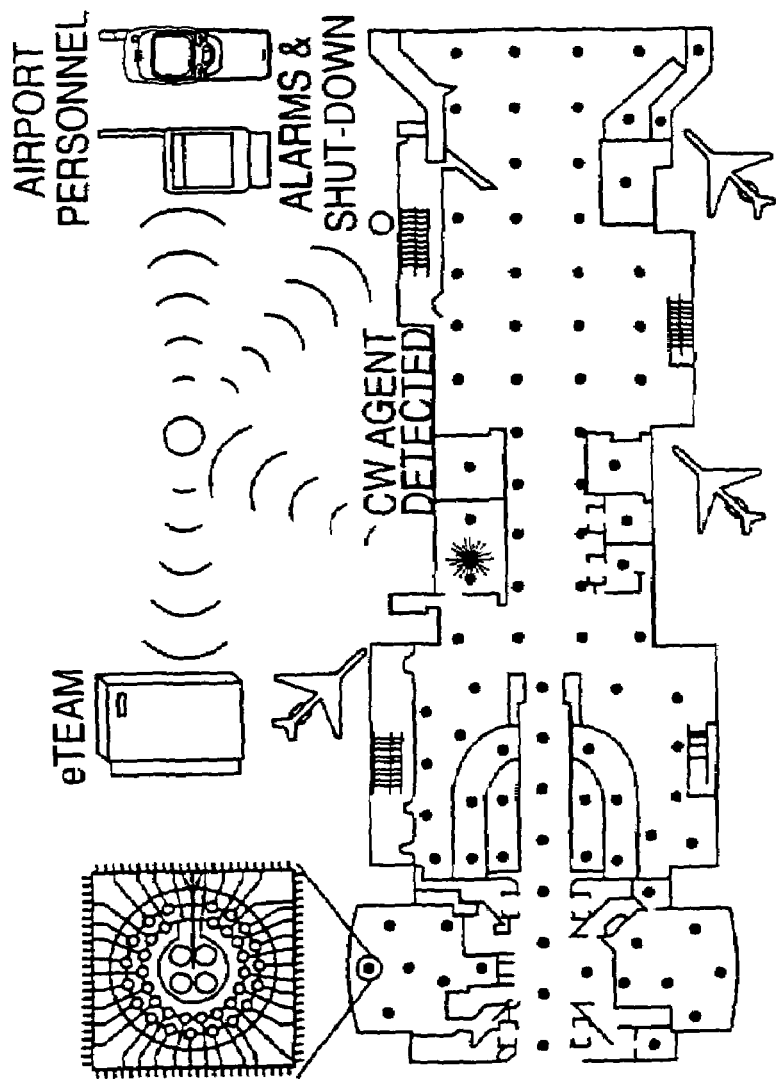
FIG. 10 illustrates a system including a distributed network of wireless sensor devices according to an embodiment of the present invention.

FIG. 10 illustrates a system including a distributed network of wireless sensor devices according to the present invention. The sensors shown can be implemented in air filtration or detection systems.

Figure 12:
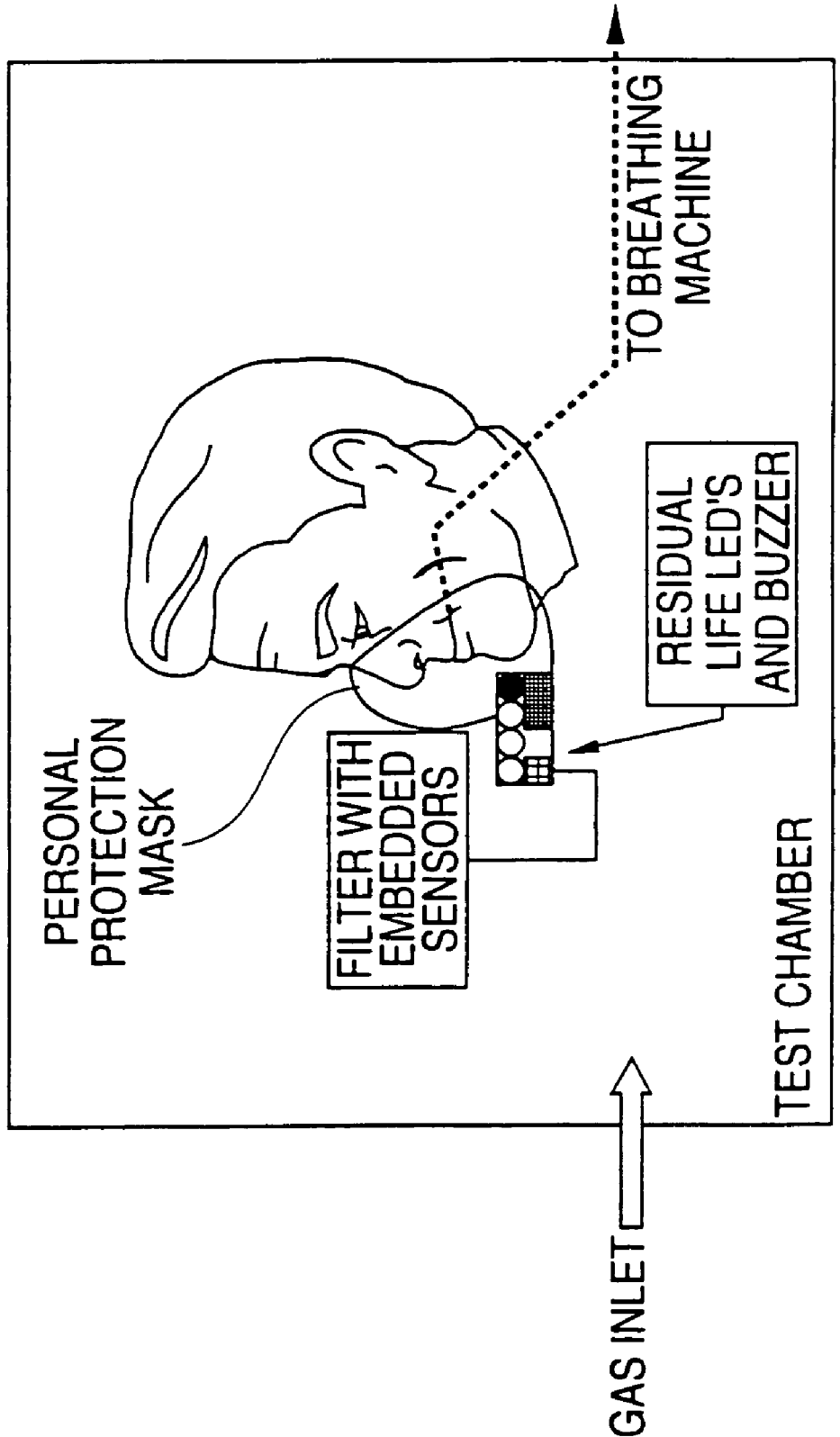
FIG. 12 illustrates a mask-based filter interface system including a detector device module according to an embodiment of the present invention.

FIG. 12 illustrates a mask-based filter interface system including a detector device module according to an embodiment of the present invention. The filter interface system communicates with the filter-based detectors and provides status/alarm output to the user based on filter status. The filter interface module is preferably configured to be mounted on the facemask and to contain the batteries, the signal processing circuitry and/or software and the visual and auditory alarms to indicate the status of the filter. Such placement allows the durable electronics to be placed in the mask and reused, thereby minimizing the operating cost (filters) of the system. Battery power usage is minimized while providing both visual and auditory cues to increase assurance of user notification in a noisy industrial environment. Size and weight is advantageously minimized using the detector devices of the present invention so as to not increase user discomfort and discourage use of the enhanced protective system.

Sensor Arrays

In certain aspects, multiple sensor types are integrated into a high density platform, preferably on a silicon chip, or other substrate material as is well known. In addition to polymer-composite and conducting polymers, useful sensor materials include, for example, nanoscale polymer composites, carbon nanotube composites, nanogold composites, intrinsically conducting polymers, sol-gel biosensors based on intrinsically conducting polymers (e.g., sol-gel encapsulated enzyme based sensors), biopolymers such as self assembling monolayer (SAM) materials and others.

Advantages of such high density arrays include the ability to construct systems with largely varying sensor properties, and the ability to include a high degree of redundancy (both features of the human system). One significant benefit of redundancy is root n noise reduction, where n is the number of identical sensor elements. For example, the inclusion of 64 identical sensors produces an overall signal to noise ratio approximately 8 times that of a single sensor (see FIG. 13). Sensor arrays that are at least an order of magnitude more sensitive than those previously produced can thus be achieved through the incorporation of high degrees of redundancy. Such redundancy also has additional benefits in terms of long-term stability and overall robustness of the system.

Figure 13:
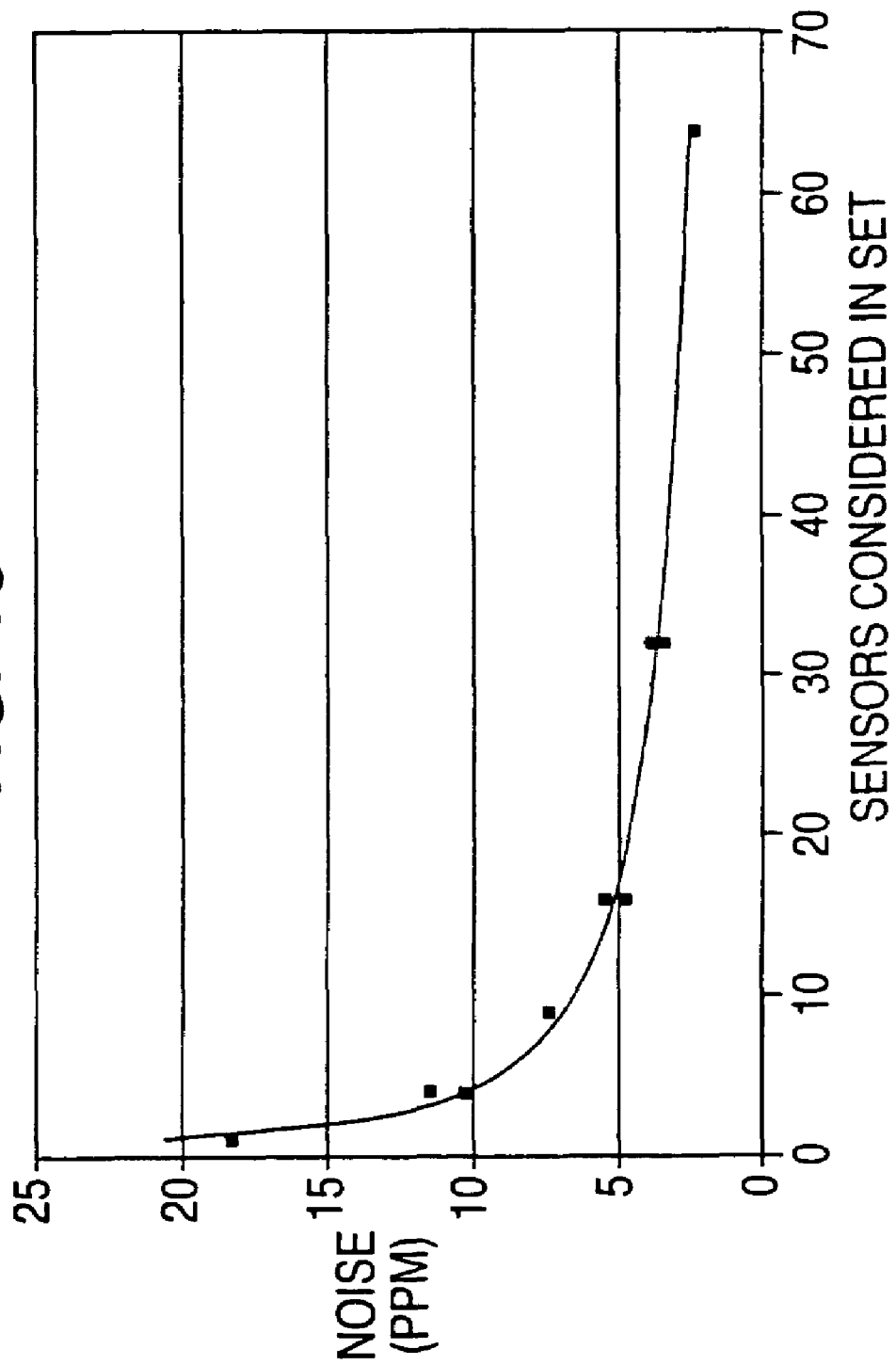
FIG. 13 shows signal to noise ratio measurements for multiple sensors.
Figure 14:
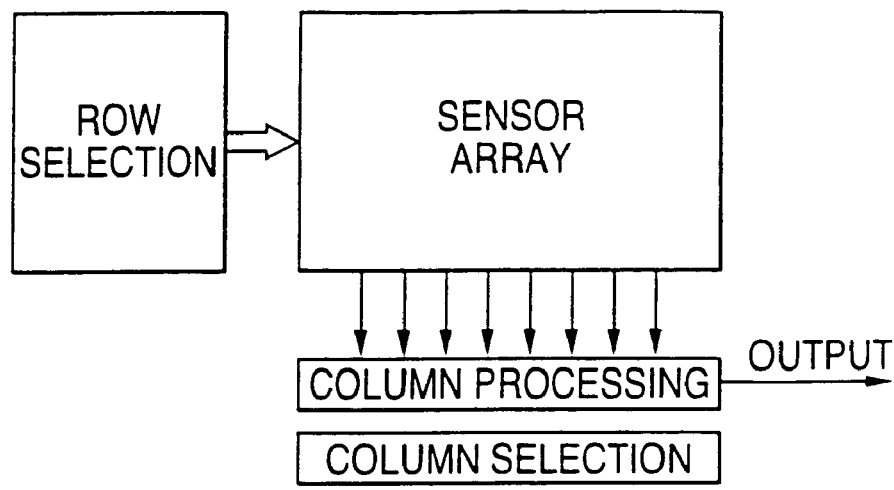
FIG. 14 shows addressing for a sensor array according to one embodiment.

According to one specific embodiment, an array comprises 900 sensor elements (e.g., 30×30), but it should be understood that arrays with fewer (e.g., one or several) or more (e.g., on the order of 10,000 sensor elements (e.g., 100×100)) or more may be implemented. In one aspect, 50 $\mu m^2$ sensor elements with a 50 $\mu m$ inter-sensor spacing are used. This yields a sensor die that is approximately 30 $mm^2$ for 900 sensor devices (approximately 1 $cm^2$ for 10,000 sensor devices). Devices with arrays preferably operate on a simple row-column addressing scheme with data being multiplexed off chip for A/D conversion and further processing, although other addressing schemes may be used. An example of addressing is shown in FIG. 13. In one aspect, sensors are read serially one at a time. As array sizes increase, more off-chip bandwidth is typically required to ensure latency between sensor readings is minimized. Sensors can then be read out in parallel, for example, a whole row at a time. Other, more advanced schemes for reading out sensors such as "address event" coding may be used. In this method "important" sensors (i.e., those that are activated) are read out first, and more frequently than other non-activated sensors.

Figure 15:
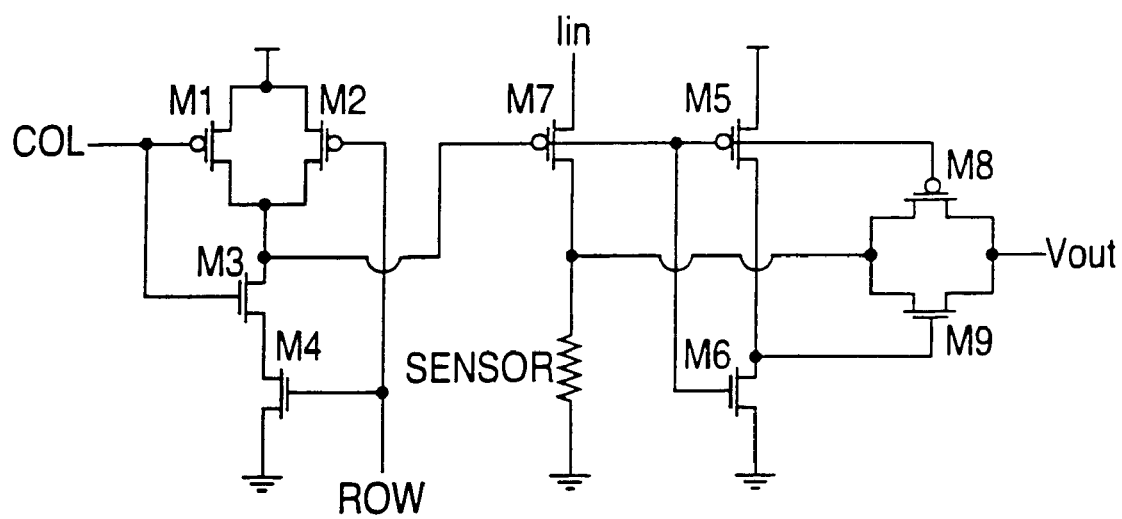
FIG. 15 shows a sensor cell according to one embodiment.

FIG. 15 shows a test unit sensor cell according to one embodiment. The cell as shown is preferably fabricated using a 2 micron CMOS process. The sensor cell includes a switch transistor and decoding logic. In one aspect, transistors at each sensor cell perform decoding, primarliy due to only two metal layers in the IC process. Circuitry M1–M4 decodes X and Y selection signals generated by shift registers on the periphery of the array. The selection signals control a switch (M7) that toggles a current (Iin) through the resistive sensor element. In one aspect of this design, only one sensor is energized at a time to reduce power consumption. To reduce noise and the switch resistance, transistor M7 occupies most of the sensor area. The decoding circuitry also selects a transmission gate (e.g., M5, M6, M8, M9) which passes the sensor voltage to a column output bus. This signal is preferably amplified and transmitted off-chip for processing, although on-chip processing may be performed.

Figure 16:
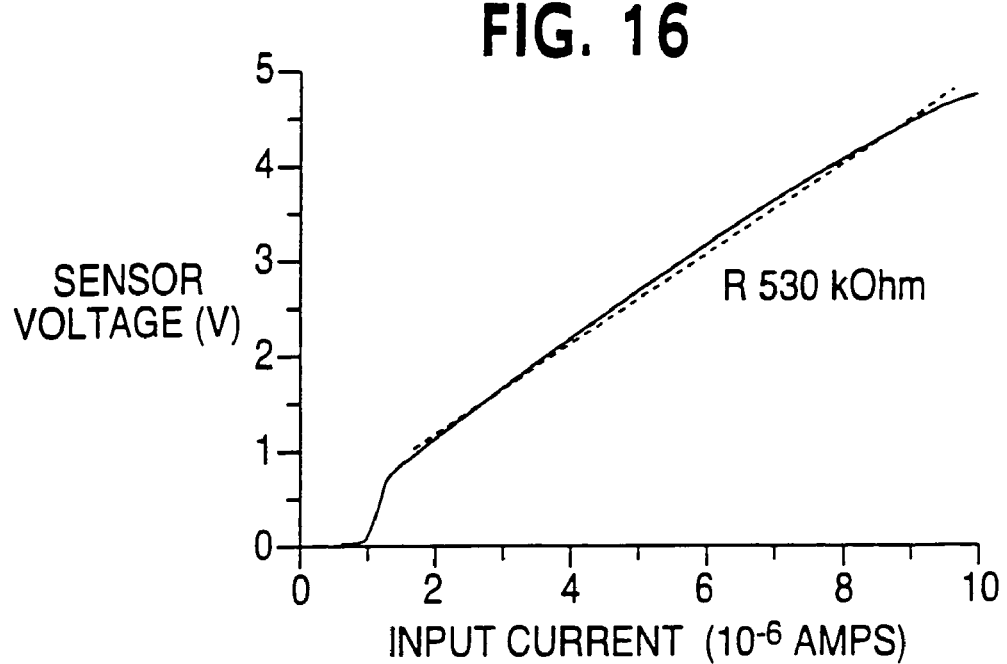
FIG. 16 shows the I–V response of the cell of FIG. 15.
Figure 17:
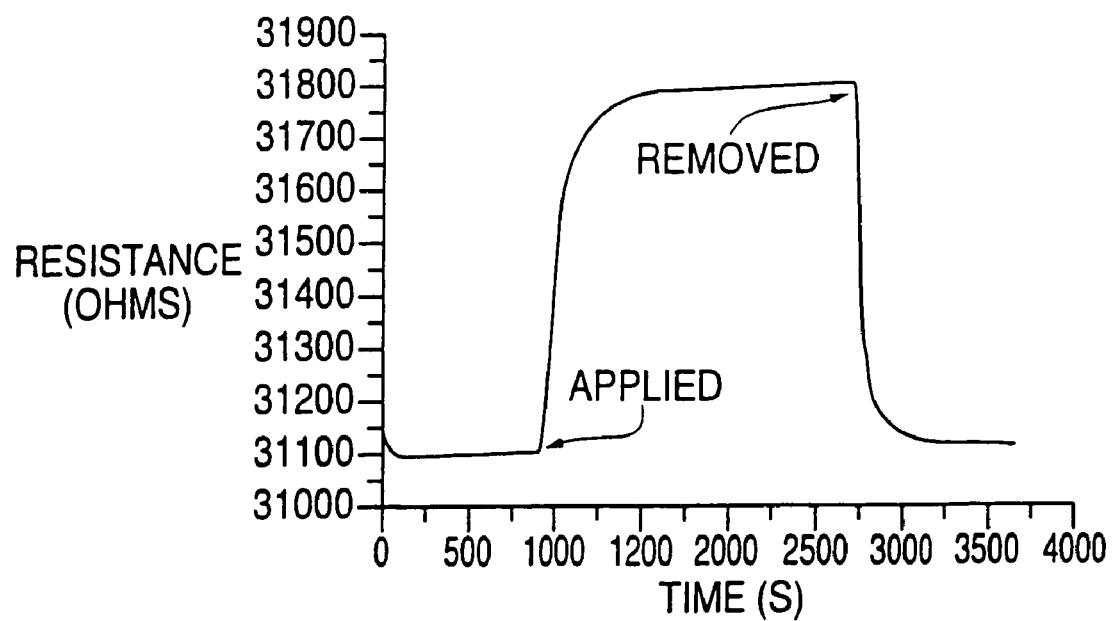
FIG. 17 shows the response of the cell of FIG. 15 to octanol.

FIGS. 16 and 17 show a typical I–V response of such a cell as shown in FIG. 15, and the response of the cell to an exposure of octanol.

Figure 18:
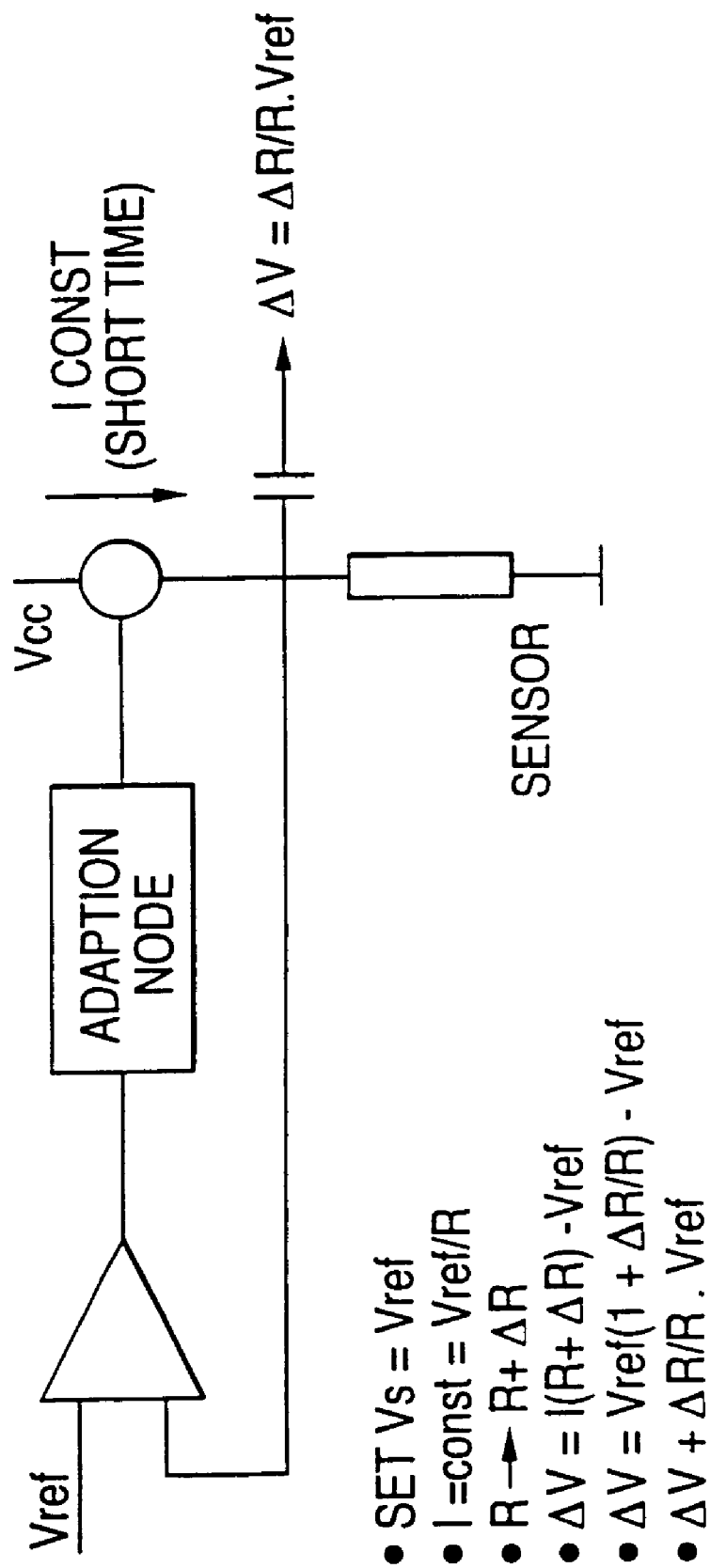
FIG. 18 shows an adaptive bias circuit according to one embodiment.

In one embodiment, analog circuitry is included to provide gain at the sensor, baseline tracking, and ratiometric sensing. Ratiometric sensing enables a direct readout of the key metric ΔR/R, that is, the change in resistance due to the chemical divided by the baseline resistance, without having to calculate this in the microprocessor. FIG. 18 shows an adaptive bias circuit 200 according to one embodiment of the present invention. Circuit 200 provides baseline tracking, ratiometric output and ac coupling in one simple analog circuit.

Although aluminum can be used for conductive traces and leads, it is preferred that an electroless gold procedure is used to produce traces and leads due to the oxidation of aluminum over time.

In certain aspects, a number of surface modified carbon black (SMCB) materials are optimized for chemical sensing. These materials can be produced using a process disclosed in U.S. Pat. No. 6,336,936, which is hereby incorporated by reference for all purposes. This process creates a direct chemical attachment of a molecule or polymer to the surface of a carbon black particle. This process results in a highly dispersible particle in the nanometer size regime (e.g., 100 nm is typical), with the chemical differentiation built into the attached organic fragment. It has been demonstrated that these materials have superior sensing properties as compared to chemically similar two-phase (carbon black dispersed in polymer) sensors.

In one aspect, four SMCB materials are used which are dispersible in chemically different solvents. These are listed in the table shown in FIG. 19. These materials have been demonstrated to be stable at the nanometer size regime and are excellent ink jetting candidates. Other useful ink-jetting materials include surface modified gold nanoparticle formulations and nanotube formulations.

Solutions and dispersions of intrinsically conducting polymers may also be deposited. Such materials preferably complement the sensing characteristics of the sensors described above. Preferred conductive polymers include polyaniline and polythiophene(s), whose structures are shown in FIGS. 20(*a*) and 20(*b*). In particular, FIG. 20*a* shows the chemical structure of polyaniline in its insulating state and its conducting state (following protonation by an acid, HX), and FIG. 20*b* shows the chemical structure of poly(3-substituted-thiophene) where R=H, or alkyl, [OX] =oxidizing agent, in its insulating state and its conducting state (following oxidative 'doping'). During the conversion of these polymers to their conducting state, an anion (or counterion) is formed either as the conjugate acid following protonation of polyaniline, or as an anion of the oxidizing agent in the case of polythiophene. It has been determined that the structure and stoichiometry of these counterions play an important role in the selectivity and sensitivity of the conductive polymer to various VOCs.

Other sensor materials include enzyme-based biogel sensors. Literature reports establish the feasibility of immobilizing enzymes and other proteins in stable, porous, silica glass matrices via an encapsulation process involving sol-gel synthesis methods. For example, as disclosed in U.S. Pat. No. 5,200,334, which is hereby incorporated by reference in its entirety, copper-zinc superoxide dimuatse, cytochrome c, and myoglobin can be immobilized using mild conditions such that the biomolecules retain their characteristic reactivities and spectroscopic properties. One key feature in synthesizing this new type of material, termed here as biogel, is the flexible solution chemistry of the sol-gel process. Research in this area has emerged rapidly throughout the world and it is now well established that a wide range of biomolecules retain their characteristic reactivities and chemical function when they are confined within the pores of the sol-gel derived matrix. Such encapsulation process is shown schematically in FIG. 21. In particular, FIG. 21 provides a schematic diagram of the sol-gel encapsulation of indicator biomolecules. "(a)" shows the formation of sol particles during initial hydrolysis and polycondensation. "(b)" shows the addition of indicator biomolecule (squiggly lined object) to the sol. "(c)" shows the growing silicate network beginning to trap the biomolecules. "(d)" shows the indicator biomolecules immobilized in the gel.

In addition to extending the sol-gel encapsulation process to numerous other enzymes and other proteins, researchers have expanded the types of biomolecular dopants to include antibodies (J. Livage, et al, *J Sol-Gel Sci. Technol.* 7, 45 (1996)) cells,(E. J. A. Pope, et al, *J Sol-Gel Sci. Technol.* 8, 635 (1997)), and even photosystems (B. C. Dave, et al, *Mat. Res. Soc. Symp. Proc.* 435,565 (1996)). It is important to emphasize that the biomolecules are physically immobilized and not covalently attached to the inorganic matrix and, therefore, the ability to incorporate biomolecules in the gel requires only that the synthetic conditions do not cause protein aggregation or denaturation (J. M. Miller, et al, *J Non-Crystalline Solids* 202, 279 (1996)). In general, this means that the sol should have minimal alcohol content and pH near 7. The inclusion of the biomolecule in the starting sol leads to a "templating" effect where the inorganic network grows around the dopant molecule. For this reason, a larger biomolecule is immobilized in the matrix while smaller molecules and ions are free to flow through the porous network. Thus, the microstructure of the sol-gel glass is tailored so that large protein macromolecules are immobilized in the matrix while analytes are free to enter and diffuse through the porous network. Physical entrapment without chemical modification preserves protein structure and functionality and protects the protein from unfolding (denaturation). The unique advantages of sol-gel immobilization include (1) an easy, simple, more universal method as chemical modification is not necessary, (2) increased durability and ruggedness as these materials can be handled without damage to the biomolecules, (3) more flexibility in sensor design as biologically active materials can be prepared as bulk monoliths or as thin films, and (4) increased stability as the biomolecules are physically, chemically, and microbially protected by a glass matrix. This increased stability due to encapsulation in a porous silica glass may be the most important benefit of the sol-gel approach. The thermal stability was also enhanced, as thermal denaturation did not occur in the silica-encapsulated sample until 95° C., whereas denaturation occurred near 65° C. in aqueous buffer. A substantial improvement in the stability of enzymes has also been observed. In studies with butyrylcholinesterase, greater than 80% of enzymatic activity was retained in sol-gel encapsulated samples after 40 days in the absence of preserving agents. In contrast, under the same conditions, enzymatic activity was almost completely lost after about 20 days in aqueous buffer. A remarkable increase in enzyme stability has been reported by Chen, et. al.,(Q. Chen, et al, *J. Am. Chem. Soc.* 120, 4582 (1998)) where the half-life of glucose oxidase at 63° C. in a sol-gel silica matrix was 200 times longer than that in aqueous buffer. These results indicate that tremendously enhanced stability of encapsulated bioindicator molecules can be achieved over other reported immobilization techniques, leading to extended device lifetimes. A further advantage of this technique is that liquid nutrient is co-encapsulated with the bioindicator molecule so that the latter can retain its vitality, but the final composition is truly a solid state device and is dry to the touch and the encapsulated materials do not leach from the matrix. Methods to control and modify the pore size have been reported so that analytes that are relatively large can flow through the matrix and interact with the immobilized bioindicator molecule.

Previous reports indicate that sol-gel materials containing physically immobilized bio-molecules can function as the active element or transducer for optical sensing applications. See, e.g., D. Avnir, et al, *Chem. Mater.* 6, 1605 (1994); E. H. Lan, et al, *Mat. Res. Soc. Symp. Proc.* 330, 289 (1994); K. E. Chung, et al, *Anal. Chem.,* 67, 1505 (1995); S. A. Yamanaka, et al, *Chem. Mater.* 4, 495 (1992); S. A. Yamanaka, et al, *J. Sol-Gel Sci. Technol.* 7, 117 (1996); and S. A. Yamanaka, et al, *J. Am. Chem. Soc.* 117, 9095 (1995).

Applications

In certain aspects, devices according to the present invention can be used to detect and analyze events and conditions in a wide variety of commercial applications including, but not limited to:

applications in industries such as utility and power, oil/gas petrochemical, chemical/plastics, automatic ventilation control (cooking, smoking, etc.), heavy industrial manufacturing, environmental toxicology and remediation, biomedicine, cosmetic/perfume, pharmaceutical, transportation, emergency response and law enforcement;

detection, identification, and/or monitoring of combustible gas, natural gas, $H_2S$, ambient air, emissions control, air intake, smoke, hazardous leak, hazardous spill, fugitive emission, hazardous spill;

beverage, food, and agricultural products monitoring and control, such as freshness detection, fruit ripening control, fermentation process, and flavor composition and identification;

detection and identification of illegal substance, explosives, transformer fault, refrigerant and fumigant, formaldehyde, diesel/gasoline/aviation fuel, hospital/medical anesthesia & sterilization gas;

telesurgery, body fluids analysis, drug discovery, infectious disease detection and breath applications, worker protection, arson investigation, personal identification, perimeter monitoring, fragrance formulation; and solvent recovery effectiveness, refueling operations, shipping container inspection, enclosed space surveying, product quality testing, materials quality control, product identification and quality testing.

Additional Sensor Types

In certain aspects, devices of the present invention may include many different sensor types in addition to, or in place of, PCS or other chemical sensors. Such additional sensor types include, for example, radiation detection (e.g., geiger, scintillation, solid state), chemical, nuclear, explosive, biological (e.g., DNA, oligonucleotide, antibody-antigen, enzyme reaction, etc) fire detection, and other sensor types. Suitable sensors for the systems and devices of the present invention can also include, but are not limited to, one or more of a conducting/non-conducting region sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, an electrochemical cell, a conducting polymer sensor, a catalytic gas sensor, an organic semiconducting gas sensor, a solid electrolyte gas sensor, and a piezoelectric quartz crystal sensor. It will be apparent to those of skill in the art that the devices of the present invention can include combinations of one or more of the foregoing sensors and sensor types.

In certain embodiments, an additional sensor can include a single sensor or an array of sensors capable of producing a second response in the presence of physical stimuli. The physical detection sensors detect physical stimuli. Suitable physical stimuli include, but are not limited to, thermal stimuli, radiation stimuli, mechanical stimuli, pressure, visual, magnetic stimuli, and electrical stimuli.

Thermal sensors can detect stimuli which include, but are not limited to, temperature, heat, heat flow, entropy, heat capacity, etc. Radiation sensors can detect stimuli that include, but are not limited to, gamma rays, X-rays, ultra-violet rays, visible, infrared, microwaves and radio waves. Mechanical sensors can detect stimuli which include, but are not limited to, displacement, velocity, acceleration, force, torque, pressure, mass, flow, acoustic wavelength, and amplitude. Magnetic sensors can detect stimuli that include, but are not limited to, magnetic field, flux, magnetic moment, magnetization, and magnetic permeability. Electrical sensors can detect stimuli which include, but are not limited to, charge, current, voltage, resistance, conductance, capacitance, inductance, dielectric permittivity, polarization and frequency.

In certain embodiments, thermal sensors are suitable for use in the present invention. Such thermal sensors include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

In other embodiments, various radiation sensors are suitable for use in the present invention. Such radiation sensors include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors. Optical sensors also detect visible, near infrared and infrared waves. In certain other embodiments, various mechanical sensors are suitable for use in the present invention and include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors.

In certain other embodiments, various chemical or biochemical sensors are suitable for use in the present invention and include, but are not limited to, metal oxide gas sensors, such as tin oxide gas sensors, organic gas sensors, chemocapacitors, chemoidiodes, such as inorganic Schottky device, metal oxide field effect transistor (MOSFET), piezoelectric devices, ion selective FET for pH sensors, polymeric humidity sensors, electrochemical cell sensors, pellistors gas sensors, piezoelectric or surface acoustical wave sensors, infrared sensors, surface plasmon sensors, and fiber optical sensors.

Various other sensors suitable for use in the present invention include, but are not limited to, sintered metal oxide sensors, phthalocyanine sensors, membranes, Pd-gate MOSFET, electrochemical cells, conducting polymer sensors, lipid coating sensors and metal FET structures. In certain preferred embodiments, the sensors include, but are not limited to, metal oxide sensors such as a Tuguchi gas sensors, catalytic gas sensors, organic semiconducting gas sensors, solid electrolyte gas sensors, piezoelectric quartz crystal sensors, fiber optic probes, a micro-electro-mechanical system device, a micro-opto-electro-mechanical system device and Langmuir-Blodgett films.

In another embodiment, the present invention includes detection using sensors as disclosed in U.S. Pat. No. 5,814,524, which issued to Walt, et al., on Sep. 29, 1998, and which is hereby incorporated by reference in its entirety. An optical detection and identification system is disclosed therein that includes an optic sensor, an optic sensing apparatus and methodology for detecting and evaluating one or more analytes of interest, either alone or in mixtures. The system comprises a supporting member and an array formed of heterogeneous, semi-selective polymer films which function as sensing receptor units and are able to detect a variety of different analytes using spectral recognition patterns. Using this system, it is possible to combine viewing and chemical sensing with imaging fiber chemical sensors.

In certain sensor network embodiments, devices of the present invention can include one or more sensors of similar or different type. Also, individual nodes, e.g., individual physical device locations, in a network of nodes can each include one or multiple sensor types. For example, a network may include one person that is wearing a (wireless) device including a single sensor type, a second person that is wearing a (wireless) device including several sensors of the same or different type, a stationary device (wireless or direct connected) that may include one or more sensors of the same or different type, and a network monitor station.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, devices according to the present invention may be used to diagnose diseases using appropriate sensor configurations and analysis algorithms. Therefore, the scope of the appended claims should be accorded the broadest interpretation so as to encompass all such modifications and similar arrangements.

What is claimed is:

1. A sensor apparatus comprising:
    two or more sensor devices;
    a processing module coupled to each of the sensor devices and configured to process signals received from each of the two or more sensor devices to determine an environmental state;
    a communication module that communicates information about the environmental state to a user; and
    a pneumatic pump system that provides vapor to the two or more sensor devices to cause the two or more sensor devices to continuously be in an operative state,
    wherein the processing module comprises:
        a digital signal processing unit that receives and processes signals output from the two or more sensor devices; and
        a memory that stores the signals processed by the digital signal processing unit.

2. The apparatus of claim 1, wherein the processor is configured to execute a first process that detects a change in an environmental condition, and a second process that identifies the origin of the change in the environmental condition.

3. The apparatus of claim 2, wherein the second process includes a pattern recognition algorithm.

4. The apparatus of claim 1, wherein the power required to operate the apparatus is less than about 1 milliwatt.

5. The apparatus of claim 4, further including one of a battery and a solar cell for supplying the power.

6. The apparatus of claim 4, further including a pick-up antenna, wherein the power is supplied by an external RF field received by the antenna.

7. The apparatus of claim 1, wherein the communication module includes one of a LED, speaker, buzzer and vibration mechanism.

8. The apparatus of claim 1, wherein the communication module includes one of a wireless interface device and a physical bus interface.

9. The apparatus of claim 8, wherein the wireless interface device includes one of an RF transmitter, an RF transceiver, an IR transmitter and an IR transceiver.

10. The apparatus of claim 8, wherein the physical bus interface includes one of an RS-232 port, a USB port and a Firewire port.

11. The apparatus of claim 1, wherein at least two of the sensor devices are polymer composite sensors.

12. The apparatus of claim 1, wherein at least one of the sensor devices is a chemical sensor.

13. The apparatus of claim 12, wherein the chemical sensor is selected from the group consisting of a polymer composite sensor and a surface modified carbon black sensor.

14. The apparatus of claim 1, wherein the apparatus has a dimension of less than about 4 square inches.

15. The apparatus of claim 1, wherein the apparatus has a dimension of less than about 1 square inch.

16. The apparatus of claim 1, wherein the sensors and the processing module are integrated on a single silicon chip.

17. The apparatus of claim 1, further including an attachment mechanism for allowing a user to wear the apparatus.

18. The apparatus of claim 17, wherein the attachment mechanism includes one of a clip and a pin.

19. The apparatus of claim 1, wherein the processing module is configured to automatically communicate information about the environmental state to an external intelligence module using the communication module.

20. The apparatus of claim 1, wherein the apparatus is used to diagnose a disease based on sampling the environment of a bodily fluid.

21. The apparatus of claim 1, wherein the processor is configured to execute a first process that detects a change in an environmental condition, and a second process that identifies the origin of the change in the environmental condition.

22. The apparatus of claim 21, further comprising a memory module configured to store various parameters associated with one or more environmental conditions.

23. The apparatus of claim 22, wherein the memory module further stores algorithms used by the first and second processes.

24. The apparatus of claim 21, wherein the communication module includes a wireless transceiver and wherein the processor is configured to automatically communicate information about environmental conditions with an external intelligence module using the communication module.

25. The apparatus of claim 21, wherein the communication module includes a physical port interface and wherein the processor is configured to automatically communicate information about environmental conditions with an external intelligence module using the communication module when the physical port interface is connected to a bus interface.

26. The apparatus of claim 25, wherein the bus interface is one of an RS-232 bus, a USB bus and a Firewire bus.

27. A wearable sensor device comprising:
    a compact housing structure;
    an attachment mechanism coupled to the housing structure;
    one or more sensors;
    an alarm module;
    a digital signal processor configured to monitor signals from the one or more sensors and provide an alarm activation signal to the alarm module in response to the detection of a threshold condition; and
    a power management system configured to operate the sensor device in one of a low power sleep mode and a high power operative mode, wherein the low power sleep mode is enabled for at least 70% of the time that the sensor device is operating,
    wherein, during the low power operative mode, the digital signal processor is woken up periodically by a wakeup signal output by the power management system to thereby cause the sensor device to enter the high power operative mode, wherein during the high power operative mode the digital signal processor scans the one or more sensors and determines whether or not an event has occurred or is occurring, and wherein the digital signal processor goes back to an inoperative sleep state and thereby causes the sensor device to reenter the low power operative mode when the digital signal processor determines that an event has not occurred or is not occurring.

28. The device of claim 27, further comprising a communication module configured to communicate with an external processor.

29. The device of claim 28, wherein the communication module includes a wireless transmitter device.

30. The device of claim 29, wherein the wireless transmitter device includes one of an RF transmitter and an IR transmitter.

31. The device of claim 27, wherein the attachment mechanism includes one of a clip and a pin for attaching the device to a user.

32. An integrated sensor apparatus, comprising:
an array of two or more sensors;
a processing module coupled to each of the sensors and configured to process signals received from each of the two or more sensors to determine an environmental state; and
a communication module that communicates information about the environmental state to a user; and
a power management system configured to operate the sensor apparatus in one of a low power sleep mode and a high power operative mode, wherein the low power sleep mode is enabled for at least 70% of the time that the sensor apparatus is operating,
wherein, during the low power operative mode, the processing module is woken up periodically by a wakeup signal output by the power management system to thereby cause the sensor apparatus to enter the high power operative mode, wherein during the high power operative mode the processing module scans the two or more sensors and determines whether or not an event has occurred or is occurring, and wherein the processing module goes back to an inoperative sleep state and thereby causes the sensor apparatus to reenter the low power operative mode when the processing module determines that an event has not occurred or is not occurring.

33. The apparatus of claim 32, further including a power source selected from the group consisting of a battery, a solar cell, an RF tag module and an IR tag module.

34. The apparatus of claim 32, wherein the communication module includes one of an LED, a vibration module and a speaker.

35. The apparatus of claim 32, wherein the apparatus is implemented in a user-wearable badge.

36. A portable sensor apparatus, comprising:
two or more sensor devices;
a processing module coupled to each of the sensor devices and configured to process signals received from each of the two or more sensor devices to determine an environmental state;
a communication module that communicates information about the environmental state to a user; and
a power supply module configured to supply power for the sensor apparatus, and
a pneumatic pump system that provides vapor to the two or more sensor devices to cause the two or more sensor devices to continuously be in an operative state,
wherein the processing module comprises:
a digital signal processing unit that receives and processes signals output from the two or more sensor devices; and
a memory that stores the signals processed by the digital signal processing unit, and wherein the lifetime of the power supply during continuous operation of the apparatus exceeds two weeks.

37. The apparatus of claim 36, wherein the lifetime of the power supply during continuous operation of the apparatus exceeds two months.

38. The apparatus of claim 36, wherein the lifetime of the power supply during continuous operation of the apparatus exceeds two years.

39. The apparatus of claim 36, further comprising a power management module configured to control power flow from the power supply module to the processor module.

40. The apparatus of claim 36, wherein the apparatus operates in a passive and continuous manner without user intervention.

41. A method of using a wearable badge detector, the badge detector having two or more sensors, a processing module coupled to each of the sensors and configured to process signals received from each of the two or more sensors to determine an environmental state, a communication module that communicates information about the environmental state to a user, and a power supply module for supplying power for the detector, the method comprising:
providing the wearable badge detector to the user
attaching the detector to the user;
activating the detector, wherein once activated, the detector operates passively and continuously in excess of one week without requiring recharging or replacement of the power supply module; and
once activated, operating the detector in one of a low power sleep mode and a high power operative mode, wherein the low power sleep mode is enabled for at least 70% of the time that the sensor apparatus is operating,
the method further comprising:
during the low power operative mode, waking up the processing module periodically by a wakeup signal output by the power supply module to thereby cause the detector to enter the high power operative mode; and
scanning the two or more sensors by the processing module and determining whether or not an event has occurred or is occurring,
wherein the processing module goes back to an inoperative sleep state and thereby causes the detector to reenter the low power operative mode when the processing module determines that an event has not occurred or is not occurring.

42. The method of claim 41, wherein the two or more sensors include polymer composite sensors.

43. The method of claim 41, wherein activating includes attaching the power supply module to the detector.

44. A portable sensor apparatus, comprising:
two or more sensor devices;
a processing module coupled to each of the sensor devices and configured to process signals received from the two or more sensor devices to determine an environmental state; and
a communication module that communicates information about the environmental state to a user; and
a pneumatic pump system that provides vapor to the two or more sensor devices to cause the two or more sensor devices to continuously be in an operative state,
wherein the processing module comprises:
a digital signal processing unit that receives and processes signals output from the two or more sensor devices; and a memory that stores the signals processed by the digital signal processing unit, and wherein the apparatus operates in a passive and continuous manner without user intervention.

45. The apparatus of claim 44, wherein the processor is configured to execute a first process that detects a change in an environmental condition, and a second process that identifies the origin of the change in the environmental condition.

46. The apparatus of claim 45, wherein the second process includes a pattern recognition algorithm.

47. The apparatus of claim 44, further comprising a power supply module configured to supply power for the sensor apparatus, wherein the lifetime of the power supply during continuous operation of the apparatus exceeds two weeks.

48. The apparatus of claim 44, further including an attachment mechanism for allowing a user to ear the apparatus.

49. The apparatus of claim 44, wherein the two or more sensors include two or more polymer composite sensors.

* * * * *